United States Patent [19]

Birkhahn et al.

[11] Patent Number: 5,420,335
[45] Date of Patent: May 30, 1995

[54] PARENTERAL NUTRIENTS BASED ON WATERSOLUBLE GLYCEROL BISACETOACETATES

[76] Inventors: Ronald H. Birkhahn, 3779 Elm Lawn Dr., Toledo, Ohio 43614; Robert J. Clemens, 511 Woodridge Cir., Kingsport, Tenn. 37663; John C. Hubbs, 507 Bell Hollow Rd., Kingsport, Tenn. 37664

[21] Appl. No.: 129,511

[22] Filed: Sep. 30, 1993

[51] Int. Cl.$^6$ .................... A61K 31/23; A61K 9/10; A23L 1/30; A23K 1/16
[52] U.S. Cl. .................................................. 560/174
[58] Field of Search .................... 560/174; 514/2, 21, 514/277, 785, 786, 943

[56] References Cited

U.S. PATENT DOCUMENTS

| | | | |
|---|---|---|---|
| 4,663,166 | 5/1987 | Veech | 424/146 |
| 4,665,057 | 5/1987 | Nelson et al. | 514/23 |
| 4,701,443 | 10/1987 | Nelson et al. | 514/23 |
| 4,997,976 | 3/1991 | Brunengraber et al. | 560/189 |
| 5,093,044 | 3/1992 | Wretlind et al. | 514/547 |
| 5,244,925 | 9/1993 | Wretlind et al. | 514/777 |
| 5,308,832 | 5/1994 | Garler et al. | 514/2 |

FOREIGN PATENT DOCUMENTS

| | | |
|---|---|---|
| 0318357 | of 1989 | European Pat. Off. |
| 0348664 | of 1990 | European Pat. Off. |
| 0366631 | of 1990 | European Pat. Off. |
| 2046091 | of 1980 | United Kingdom |
| WO90/02548 | 3/1990 | WIPO |

OTHER PUBLICATIONS

R. H. Birkhahn et al, J. Nutrition, 109, 1168 (1979).
S. A. Kripke et al, J. of Surgical Research, 44, 436 (1988).
R. H. Birkhahn et al, J. of Surgical Research 47, 427 (1989).
S. Tanaka, J. of the Osaka City Medical Center, 38, 781 (1989).
T. Nishihata et al., Chem. Pharm. Bull., 32 2025 (1984).
T. Nishihata et al., Chem. Pharm. Bull., 72, 280 (1983).

*Primary Examiner*—Arthur C. Prescott
*Attorney, Agent, or Firm*—Mark A. Montgomery

[57] ABSTRACT

Novel parenteral nutrient compositions are disclosed. These compositions are sterile aqueous solutions containing an effective amount of at least one glycerol bisacetoacetate of the formula:

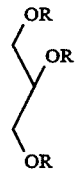

wherein one R group is hydrogen, and two R groups are $-(COCH_2COCH_3)$. These compositions are useful as a substitute for glucose in intravenous feeding.

7 Claims, 5 Drawing Sheets

PARENTERAL NUTRIENTS BASED ON WATERSOLUBLE GLYCEROL BISACETOACETATES

The present invention relates to parenteral nutrient compounds that are glycerol esters of acetoacetic acid, more particularly watersoluble glycerol bisacetoacetates.

BACKGROUND

Parenteral nutrients are administered in peripheral or central veins to supplement a patient's diet. Total parenteral nutrition is a recent advance in the maintenance of patients having an impaired gastrointestinal capacity. Such patients may have lost the use of a large portion of their intestinal tract either permanently or due to surgical intervention as may be required in cancer or Crohn's disease, or temporarily as a result of chemotherapeutic drugs or in the treatment of diverticulitis. Total parenteral nutrition is utilized as an adjunct therapy for the critically ill patient who has a generally increased metabolic rate and is unable to eat. The intent of the nutritional support is to prevent the loss of body nitrogen and the resulting complications of multiple organ failure, infection and increased chances of morbidity and mortality.

The energy source most commonly used for intravenous feeding has been glucose because carbohydrates are important for oral diets. However, glucose has not been as effective as was originally anticipated, and more importantly, the route of administration bypasses the normal digestive regulatory mechanisms for controlling blood sugar. Thus, continued intravenous administration (i.v.) of glucose generally results in high blood glucose levels which may have adverse consequences to the patient (particularly diabetics). Additional problems which can arise from i.v. glucose administration include fatty liver, respiratory stress, immune function inhibition, increased insulin secretion and undesirable metabolic regulation. Furthermore, skeletal muscle tissue is not well protected from degradation upon glucose administration to patients with trauma.

Due to these complications, it has been impossible to intravenously administer all the nutritional needs of the human body. This shortcoming poses a formidable problem to clinicians who must attempt such parenteral support. The problem is not merely one of administering a correct amount of calories and nutrients, but rather deals with providing these nutrients in a form which will suppress the breakdown of body proteins (catabolism) such as muscle tissue. This problem extends to trauma patients, where the goal is to provide supplemental energy sources to meet the increased energetic demands of the healing process.

Attempts have been made to find substitutes for glucose that do not instill an insulin response and that do not break down the body proteins. Substrates with metabolic properties very similar to glucose but lacking a significant insulin response are the so-called ketone bodies, 3-hydroxybutyrate and acetoacetate. U.S. Pat. No. 5,093,044 discloses water insoluble glycerol esters containing two or three acetoacetyl groups or two or three hydroxybutyryl groups. These compounds are water insoluble and thus must be administered enterally or parenterally in emulsion form. Other glyceride esters disclosed in this patent are based on pyruvic acid and lactic acid. The following publications disclose the water soluble monoglyceride of acetoacetic acid that is metabolized in vivo. European Pat. Application 0348664 (1990); R. H. Birkhahn et al., J. Nutrition, 109, 1168 (1979); S. A. Kripke et al., J. of Surgical Research, 44, 436 (1988); R. H. Birkhahn et al., J. of Surgical Research, 47, 427 (1989); S. Tanaka, J. of the Osaka City Medical Center, 38, 781 (1989).

WO90/02548 discloses an energy substrate containing alpha-hydroxycarboxylic acid and glycerol ester.

U.S. Pat. No. 4,997,976 discloses the use of 1,3-butanediol acetoacetate in parenteral oral nutrition.

U.S. Pat. No. 4,665,057 discloses a variety of nutrient monoesters of saccharides and monoglycerides containing fatty acids of four to ten carbon atoms.

U.S. Pat. No. 4,701,443 discloses certain nutrient polyesters based on dibasic acids such as succinic acid which may also contain moieties such as sugars, acetoacetyl groups and 3-hydroxybutyryl groups.

T. Nishihata et al., Chem. Pharm. Bull., 32,2025(1984); T. Nishihata et al, Chem. Pharm. Bull., 72,280(1983); and JP Kokai 113,723(1980) disclose compounds such as glycerol 1,3-diacetoacetate, 1,2-isopropylideneglyceryl 3-acetoacetate, and 2,3-isopropylidene-1-acetate that enhance the absorption of certain agents in the intestine.

In light of the above, it would be very desirable to be able to produce and use water soluble non-glucose based parenteral nutrients that are at least as effective as glucose in supporting body weight with less of an insulin response and less protein degradation.

SUMMARY OF THE INVENTION

The present invention relates to a parenteral nutrient solution that comprises a sterile aqueous solution of an effective amount of at least one glycerol bisacetoacetate of the formula:

wherein one R group is hydrogen, and two R groups are $-(COCH_2COCH_3)$.

The present invention also relates to a process for the administration of the above parenteral nutrient solution wherein the solution is introduced into a central or peripheral vein.

DETAILED DESCRIPTION OF THE INVENTION

Applicants have unexpectedly discovered novel aqueous parenteral nutrient compositions. These novel parenteral nutrient compositions can be substituted for glucose, providing the energy requirement of the body receiving intravenous feeding without the complications caused by glucose infusion.

The novel parenteral nutrient compositions of the present invention preferably comprise sterile aqueous solutions of an effective amount of at least one glycerol bisacetoacetate of the formula:

wherein one R group is hydrogen and two R groups are $(COCH_2COCH_3)$. This is specifically 1,3-bisacetoacetyl glycerol, 1,2-bisacetoacetyl glycerol, and mixtures thereof.

The parenteral nutrient solution of the present invention preferably contains about 1 to 50 weight percent of at least one glycerol bisacetoacetate, more preferably about 1 to 25 weight percent, with a weight percent of about 5 to 15 being most preferred. Amounts below about 1% are too dilute to dramatically affect the caloric needs of a body whereas the upper limit is only affected by the ability to administer the liquid, unless the administration is in a peripheral vein. Amounts significantly in excess of 12.5% can cause damage to peripheral veins. Amounts significantly, in excess of 12.5 weight % can however be conveniently used when the parenteral nutrient is administered via a central vein.

The compositions of the present invention can also contain a minor amount of trisacetoacetyl glycerol, such as about 1 to 30 weight percent. Surprisingly this compound is rendered water soluble when in the presence of a glycerol bisacetoacetate.

The glycerol bisacetoacetates in the solution according to the present invention preferably contain at least 50% of the 1,3 isomer.

The novel compounds or compositions of the present invention are useful in a parenteral nutrient composition that comprises a sterile aqueous solution of an effective amount of at least one of the above glycerol bisacetoacetates.

These novel compounds or compositions are useful in stabilizing or increasing patient weight, reducing nitrogen loss and effecting other metabolic and physiological improvements in the clinical state of the patient. For parenteral administration, the selected compound or mixture of compounds is dissolved in an aqueous solution at the desired concentration. If necessary, the compound need not be dissolved in an aqueous solution at all until reconstitution before administration. This, however, is not as commercially desirable as supplying a ready-to-use solution.

The solution for administration frequently will be mixed with other nutrients or with drugs. Such other nutrients include nitrogen sources such as amino acids, essential fatty acids such as linoleic or linolenic acid, vitamins, minerals, and electrolytes including trace elements. Other calorie sources such as carbohydrates or lipids will not ordinarily be needed but can be supplied as required clinically. The amino acids are mixed with the compounds prior to or after sterilization. A mixture of essential amino acids nutritionally balanced will ordinarily be sufficient, although nonessential amino acids can be included. The proportions can be adjusted for special disease states, e.g., inborn errors of metabolism, in accord with known practice. Supplemental nutrients should also be selected to avoid adverse effects on the compounds during sterilization and/or storage. The pH can range about from 5.5 to 7.5. Other conventional additives such as antioxidants, buffers and the like can be included as well.

The solutions are packaged in conventional parenteral solution containers, either glass or thermoplastic flexible bags. Such containers are sterile sealed and contain means for connecting with the patient's circulation, either alone or in concert with other devices. Typically, the means for connecting with the patient's circulation will be a frangible member associated with the container which is adapted to enter into fluid connection with an administration set. Such sets also are well known.

The solutions usually are parenterally administered by infusion into a central or peripheral vein. The compound concentration is not critical. However, it should not be so low as to introduce undue amounts of water into the patient, nor so high as to cause peripheral vascular irritation. Generally an osmolarity below about 600 mOsm is satisfactory for peripheral parenteral infusion. Naturally, compounds containing the greatest number of calories per osmol are preferred. Less advantageously, the solution can be infused at a rate sufficient to maintain the nutritional status of the patient in concert with the intake of other nutrients. Infusion will be ordinarily about from 25 to 40 Kcal/Kg patient weight/day, but the amount administered parenterally will depend upon the patient's oral intake of the compounds or other nutrients.

The compounds herein have the advantage of a higher molar energy content than glucose.

The process of producing the glycerol bisacetoacetates comprises reacting at a temperature of about 0° to 180° C. an unprotected glycerol and an acetoacetate ester or acetoacetate precursor to produce glycerol bisacetoacetates of the formula:

wherein one R group is hydrogen and two R groups are -(COCH$_2$COCH$_3$).

The acetoacetate ester reacted above is preferably of the formula R'OCOCH$_2$COCH$_3$ wherein R' is aryl, alkyl or substituted alkyl. R' is preferably t-butyl, ethyl or methyl. Examples of suitable acetoacetate esters or acetoacetate precursors include tert-butylacetoacetate, methylacetoacetate, ethylacetoacetate, diketene, and 2,2,6-trimethyl-4H-1,3-dioxin-4-one (the diketene acetone adduct). For economic reasons diketene is the most preferred reagent for acetoacetylation of glycerol.

The process of the present invention is optionally conducted in an organic solvent. Specific examples of suitable organic solvents include methyl acetoacetate, ethyl acetoacetate, ethyl acetate, butyl acetate, and mixtures thereof.

The glycerol bisacetoacetate reaction product can be purified by aqueous extraction such as dissolving the product in ethyl acetate and extracting with distilled water.

Specific preparatory schemes for the most preferred compound of the present invention and two comparative compounds are illustrated below in Schemes 1, 2, and 3 respectively.

SCHEME 1

The preparatory scheme for 1,2- and 1,3-bisacetoacetyl glycerol is shown in below.

1,2- and 1,3-bisacetoacetyl glycerol, which are surprisingly water soluble, can be made directly from diketene. It is also possible to use tert-butyl acetoacetate instead of diketene to provide the desired acetoacetyl derivative. In this case, suitable reaction temperatures include about 70° C. to about 180° C. A simple aqueous extraction can be used to enrich the reaction product in 1,2- and 1,3-bisacetoacetyl glycerol (See Examples). Small amounts of trisacetoacetyl glycerol (insoluble by itself in water) are surprisingly solubilized in water when in the presence of 1,2- and 1,3-bisacetoacetyl glycerol.

Scheme 1

1a + 1b = 80% of purified mixture
1a/1b = 2.6/1

Compound 1

Scheme 2
The preparatory scheme for 1-acetoacetamido-2,3-propane diol is illustrated below and in Example 3.

Scheme 3

The preparatory scheme for partially reduced pentaacetoacetyl-glucose is illustrated above in Examples 5 and 6.

EXAMPLES

In the examples that follow Example 1 describes the preparation of 1,2- and 1,3-bisacetoacetyl glycerol. Example 2 describes the unexpectedly high nutrient activity of 1,2- and 1,3-bisacetoacetyl glycerol as a parenteral nutrient. Example 3 describes the preparation of 1-acetoacetamido-2,3-propane diol and Example 5 and 6 describe the preparation of partially reduced pentaacetoacetyl glucose. Examples 4 and 7 demonstrate that 1-acetoacetamido-2,3-propane diol and partially reduced pentaacetoacetyl glucose are ineffective as parenteral nutrients. Examples 3-7 thus serve as comparative examples which further demonstrate how unexpected 1,2- and 1,3-bisacetoacetyl glycerol are as water soluble parenteral nutrients.

The following examples are intended to illustrate the present invention and are not intended to limit the reasonable scope thereof.

Experimental

Proton and carbon nuclear magnetic resonance (NMR) spectra were recorded on a Varian Gemini 300 NMR instrument operating at 300 MHz in proton mode and 75 MHz in carbon mode. Spectra were plotted using Varian version 6.3A software. All spectra are referenced to TMS at 0 ppm unless otherwise noted. For the proton NMR spectra of acetoacetates, the ratio of the acetoacetate methyl peak(s) at ca. 2.2 to 2.3 ppm to the methyl peak(s) at ca. 1.9 to 2 ppm (enolic methyl) has been found to provide a sensitive measurement for the percent enol content in solutions of acetoacetates. Unless otherwise noted, where percent enol composition is indicated, the NMR tube containing the solution of acetoacetate in the indicated solvent has been allowed to equilibrate at room temperature for a minimum of 24 hours. For proton spectra, a pulse delay of 10 seconds was utilized to assure accurate integration. Proton NMR spectra were typically run at a concentration of 5 to 50 mg experimental compound per gram of solution. Proton and carbon coupling constants were measured directly from line spacings. Thus, in the proton NMR for ABX spin systems the reported $J_{ax}$ and $J_{bx}$ may be slightly in error when $V_a-V_b/J_{ab}$ approaches 2. Carbon NMR spectra were typically run at a concentration of 50 mg per gram of solution. Reported chemical shifts were obtained from fully proton decoupled spectra. For the carbon spectra of single isomers (not mixtures of diastereomers) both multiplicities and carbon-proton coupling constants are reported and were obtained by turning the decoupler off prior to data acquisition. Multiplicities for large one bond couplings (>100 Hz) are reported in capital letters while multiplicities for small long range couplings are reported in lower case letters. Coupling constants are reported as measured. The accuracy of reported coupling constants is assumed to be no less than three times the digital resolution. The linewidth of TMS at half height (resolution enhanced) is reported for all cases in which the line width exceeded six times the digital resolution.

Infrared spectra were recorded on an Nicolet 5DX Spectrophotometer and major peak minima are reported in reciprocal centimeters (cm −1). This instrument is capable of typical resolutions of less than 4 reciprocal centimeters. Infrared spectra were recorded from films (for oils) or KBr pellets for crystalline materials.

Mass spectra (MS) were obtained using a VG Analytical Ltd. Model ZAB-1F Mass Spectrometer in EI (electron impact), fast atom bombardment (FAB, Xenon gas) or FD (field desorption) mode. Gas chromatography-mass spectroscopy (GCMS) and accurate mass measurements (exact mass) were conducted using a VG 70-SEQ instrument equipped with a 30 meter DB5 capillary column (J and W Scientific) using helium carrier gas.

Trace metal analyses were performed by Atomic Absorption (Na) or by ICP (inductively coupled plasma for Fe, Al or Ni) on a Perkin Elmer ICP/6000 instrument. Elemental Analyses (C,H,N) were performed on a Carlo Erba Model 1106 Elemental Analyzer.

Example 1: Preparation of Glycerol bis-acetoacetate (Compound 1)

Diketene (250 ml) was slowly added by dropwise addition over a four hour period to a mechanically stirred solution of glycerol (1477 g) and dimethylaminopyridine (DMAP, 0.25 g). A room temperature water bath was applied to the external surface of the reactor in order to maintain the reaction at a temperature of between 20° and 30° C. The reaction mixture was left to stir overnight at room temperature. On the following four working days, additional charges of dimethylaminopyridine (added and dissolved first) and then diketene were added to the stirred reaction vessel as described above (charge no. 2; 0.25 g DMAP, 500 ml diketene: charge no. 3; 0.25 g DMAP, 500 ml diketene: charge no. 4; 0.1 g DMAP, 740 ml diketene: charge no. 5; 0.1 g DMAP, 500 ml diketene). The final molar ratio of added diketene to added glycerol was 2.01 to 1.

HPLC analysis of the crude reaction mixture revealed that the major product was bisacetoacetyl glycerol with lesser amounts of trisacetoacetylglycerol and monoacetoacetin.

A portion of the crude reaction product (3600 g) was dissolved in approximately 6 liters of ethyl acetate and extracted with distilled water (3×3 L) to provide a first aqueous fraction and again extracted with water (6× 3 L) to provide a second aqueous fraction. Analysis of the aqueous extracts by HPLC indicated that essentially all of the monoacetoacetin contained in the crude reaction product was removed in the first aqueous fraction. Using a freeze-dryer, water was removed from the second aqueous fraction until constant weight was achieved (1029.5 g, ca. 30%). This material was tested without further purification for efficacy as a parenteral nutrient.

Proton NMR analysis of this second aqueous fraction indicated the following composition: 1,3-bisacetoacetyl glycerol—58 mole %, 1,2-bisacetoacetylglycerol—22 mole %, trisacetoacetylglycerol 14 mole %, monoacetoacetin(mixture of 1 and 2-isomers)—ca. 6 mole %.

Karl Fischer: Water=0.26%

Elemental Analysis: (Calculated for the above molar composition) Predicted for $C_{11.32}H_{16.32}O_{7.16}$: C, 50.93; H, 6.16 Predicted for $C_{11.32}H_{16.32}O_{7.16}+0.26\%$ water: C, 50.80; H, 6.17 Found: C, 50.53; H, 6.32

In order to simplify spectral analysis (and to allow for subsequent analysis of the complete product mixture-vide supra) the major HPLC peak from the above sample was collected (Vydac TP1010, 10 mmID×25 cm semipreparative C-18 reverse phase column; 100 mg injection in 2 ml water with a gradient from 0 to 20% acetonitrile over 10 minutes after an initial isocratic period of 10 minutes at 0% acetonitrile-remainder water and a flow rate of 6 ml/min). The eluate containing the major component (84.8 mg, as a mixture of the 1,2 and 1,3 isomer of bisacetoacetyl-glycerol) was lyophilized and analyzed by NMR and field desorption mass spectrometry.

$^1$H NMR (1,3-isomer=75% of mixture) (CDCl$_3$, digital resolution=0.095 Hz): keto form: 4.35–4.19 (unresolved, 4 H), 4.2–4.1 (m, 1H), 3.55 (q, J=0.4, 4H), 2.58 (bs, OH), 2.29 (t, J=0.4, 6H)

$^1$H NMR (1,2-isomer=25% of mixture) (CDCl$_3$, digital resolution=0.095 Hz ): keto form: 5.25–5.17 (m, 1H), 4.41–4.25 (m, 2H), 3.84 (dd, J=12.3, 4.2, 1H), 3.74 (dd, J=12.3, 5.6, 1H), 3.55 (unresolved, 2H), 3.51 (q, J=0.4, 2H), 2.58 (bs, OH), 2.29 (unresolved, 3H), 2.28 (t, J=0.4, 3H)

$^{13}$C NMR (1,3-isomer) (CDCl$_3$, digital resolution=0.502 for chemical shifts, 0.205 for coupling constants): 201.0 (Sm), 166.9 (Sm), 67.5 (Dm, J=146), 65.6 (T and apparent q, J=148.9, 3), 49.9 (Tq, J=130.4, 1.5), 30.3 (Q, J=128.2)

$^{13}$C NMR (1,2-isomer) (CDCl$_3$, digital resolution=0.502 for chemical shifts, 0.205 for coupling constants): 201 (Sm), 200 (Sm), 166.9 (Sm), 166.5 (Sm), 73.1 (Dm, J=149), 62.9 (T-unresolved), 60.9 (Tm, J=143.8), 49.7 (Tq, J=130.6, 1.5), 49.6 (Tq, J=130.5, 1.4), 30.3 (two carbons, Q, J=128.2)

FDMS: M+1=261

Example 2: Evaluation of 1,2- and 1,3-bisacetoacetylglycerol (Compound 1) as a Parenteral Nutrient A 560 g. sample of material from Example 1 analyzed to contain ca. 58 mole % of 1,3-bisacetoacetylglycerol (1a), ca. 22 mole % of 1,2-bisacetoacetylglycerol (1b), ca. 14 mole % trisacetoacetylglycerol, and approximately 6 mole % of monoacetoacetylglycerol. The energy density for the mixture was estimated to be 4.33 kcal/gram based on an estimate of each component of the mixture having the same estimated energy density as indicated in the attached table 6. The heats of combustion are not the same as metabolic energy and our data has suggested that the loss of acetoacetate in the primary positions (1 or 3) is more rapid than when acetoacetate is in the secondary position (2). This compound was infused at a rate which was estimated to provide 27 kcal/day if all of the compound was oxidized. It must be realized that such a load, though high in energy, might not be tolerated by the rat depending on the rate of acetoacetate release. This compound mixture provides on the average more energy from acetoacetate than does the monoglyceride since the ratio of glycerol to acetoacetate is 1:1 for the monoglyceride and 1:2 for the diglyceride. Calculated energy content for isosmotic solutions of mono- or di- glyceride are 228 and 337 kcal/liter which illustrates that increasing the molecular size of the substrate increases the energy per molecule.

Protocol

Forty-eight male Sprague-Dawley rats with body weights 175 to 200 g were purchased from Harlan Sprague-Dawley, Indianapolis, Ind. and kept at least 3 days prior to beginning any form of pretreatment or treatment. Rats were located in a limited access area which was air conditioned and had controlled 12 hour light-dark cycles. Water was available ad libitum at all times. Rats were housed 4 per cage until pretreatment when they were transferred to individual metabolic cages in which the rat lived throughout the remainder of the experimental period. Pretreatment consisted of inducing general anesthesia with ketamine hydrochloride (10 mg/100 g body weight) and sewing a light weight plastic button on to the nape of the rats neck. The rats were placed in individual metabolic cages adapted to permit continuous intravenous infusion. Rats were allowed 7 days to recover from the stress of having the back button attached, and each rat was monitored for body weight changes and food intake. Any rat which did not exhibit satisfactory growth during this 7 day pretreatment was excluded from testing. Rat diet consisted of solid rat chow for 4 days and complete oral liquid diet (rat diet #711C from Bioserve Inc., Frenchtown, N.J.) for 3 days.

On day 7, each rat was again given general anesthesia as above and surgically prepared for continuous intravenous infusion by placing a silastic catheter in the right external jugular vein. The outer skin was prepped by cleaning with alcohol (ethanol) and betadine solution. A small incision was made in the neck to externalize the superficial jugular vein. The vein was ligated proximally to an opening cut into the vessel, and the silastic catheter threaded into the superior vena cava. The vein was then ligated dorsally to the catheter. The catheter was threaded subcutaneously to the back of the neck where it exited the skin into a wire catheter protector which was anchored to the back button and to a swivel mounted above the cage. Neck skin was closed with staples, and rats were returned to their individual cages. Rats were allowed a minimum of 3 days to recover from surgery. Catheters were kept open by infusing 0.9% saline at 25 mL/day, and rats were fed the liquid oral diet ad libitum. Body weights were measured daily. Any rats which did not exhibit satisfactory recovery were excluded from further treatments.

On day zero, rats were divided into 3 weight matched groups which were distinguished by receiving one of three solutions. Experimental compound was prepared by dissolving 12.5 grams in 100 mL total volume of 0.9% saline and passed through a 0.22 micron filter for sterilization. This solution contained 54 kcal/100 mL and was infused at 50 mL/day to provide 27 kcal/day which is 50% of the rats estimated energy requirement. The second group was infused with a 16% glucose solution which provided isocaloric intake. Group three was infused with 50 mL/day with 0.9% saline solution. All rats were switched to a low energy liquid diet which contained similar amounts of protein, vitamins, electrolytes, and minerals but only 50% of the nonprotein energy. Rats infused with experimental compound were fed the low energy diet ad libitum. Glucose and saline infused rats held their low energy diet and infusion started 24 hours later than the experimental infused rats because their volume of oral food offered was based on the voluble of oral food consumed the previous day by the experimental infused rats. Thus, glucose and saline infused rats were fed the same volume of oral food as that eaten by their matched rats in the experimental group. Day 1 in the results for the glucose and saline infused rats was occurring on the same date as day 2 in the results for the experimental compound infused rats.

Infusate volume, oral food intake, body weight and urinary volume and total nitrogen were monitored daily for each rat. Infusate volume and food intake were determined by weighing the appropriate container at the start and end of each 24 hr. period. Measurements were recorded between 9 and 10 AM each day. At the end of the 7th day, rats were sacrificed, and blood and liver were harvested. Plasma was separated for measurement of free fatty acids, glucose, and ketone bodies. Liver was weighed and a sample was fixed in buffered formalin for gross histology.

The data were analyzed for significance by the one-way analysis of variance with repeated measures and comparing the effect of dietary treatment on each day. Tukey's post-hoc test was used to determine which treatments were significantly different. The null hypothesis was concluded invalid if $p \leq 0.05$. The analysis of variance was computed on a SAS statistical package.

For the figures which follow, each point represents the average of all rats in a particular group.

Results

A total of 32 rats were started with intravenous infusion and 11 were lost from a variety of complications. Three rats died before the infusion of any intravenous nutrient. Five rats on the experimental compound died from causes unknown (possibly too much acetoacetate for the system of these particular rats). One rat on the experimental compound was sacrificed because of a leaking catheter. Two rats (one on glucose and one on the experimental compound) were deleted from the study at the end because both were bloated in the neck region which suggested subcutaneous rather than intravenous infusion. The final rat count was 7 rats infused with experimental compound, 7 rats infused with glucose, and 7 rats infused with saline. The final data are averages from these numbers.

Figure 1:
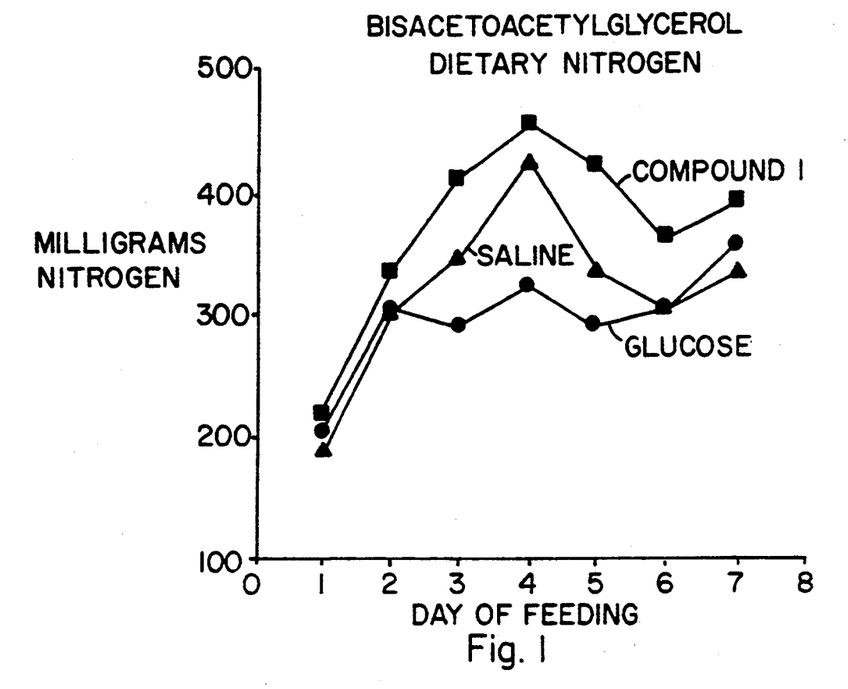
FIG. 1 shows the dietary nitrogen intake in milligrams for three groups of rats that were infused with Compound #1 (mixture of mostly 1,3- and 1,2-bisacetoacetyl glycerol), glucose, or saline over a seven day period.

Dietary nitrogen intake for individual rats is listed in table 1 and summarized for each group in FIG. 1. All rats were offered similar amounts of oral dietary nitrogen and experimental compound infused rats were fed ad libitum. Other rats were offered similar amounts as the experimental compound infused rats ate. FIG. 1 shows that there were no differences in dietary nitrogen intake among the three groups.

Figure 2:
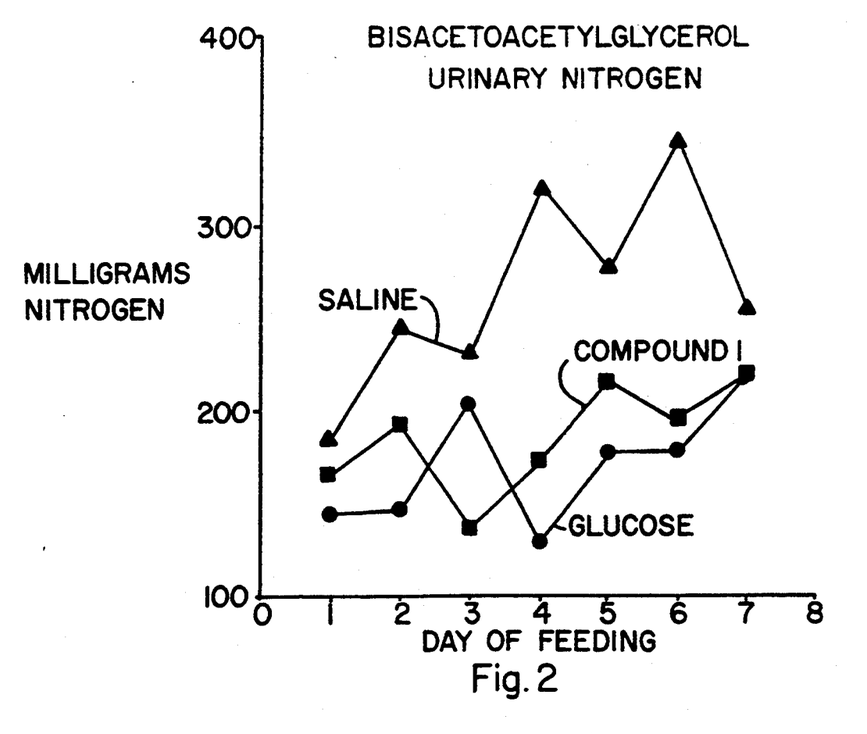
FIG. 2 shows the daily urinary nitrogen losses in milligrams for three groups of rats that were infused with Compound #1, glucose, or saline over a seven day period.

FIG. 2 illustrates the daily urinary nitrogen losses over 7 days of treatment. The individual rat data is presented in table 2. The urinary nitrogen loss pattern is quite different from the dietary nitrogen intake data. Saline infused rats lost much more nitrogen in the urine than did either of the other two groups of rats. Glucose and the experimental compound had a similar affect on restricting urinary nitrogen losses.

Figure 3:
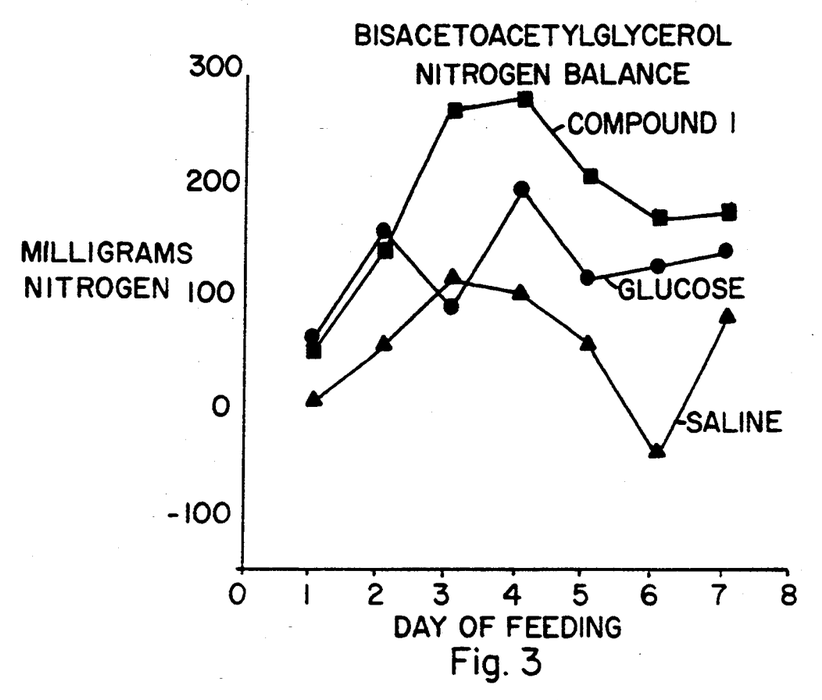
FIG. 3 shows the difference between dietary nitrogen intake and urinary nitrogen output in milligrams, which is nitrogen balance, for three groups of rats that were infused with Compound #1, glucose, or saline over a seven day period.

FIG. 3 illustrates the difference between oral intake and urinary nitrogen output which is termed nitrogen balance. It is representative of nitrogen balance because urinary nitrogen is the major route for body loss of nitrogen. Data for individual rats is listed in table 3. Saline infused rats showed a zero nitrogen balance with a tendency toward negative. The other two groups had positive nitrogen balances which ranged around +100 mg/day for glucose infused rats and around +200 mg for experimental compound infused rats. Our previous work has indicated that between 100 and 150 mg Nitrogen/day retention is needed to demonstrate growth in body weight. This data would suggest that the rats fed the experimental compound gained weight and that rats fed glucose maintained weight.

Figure 4:
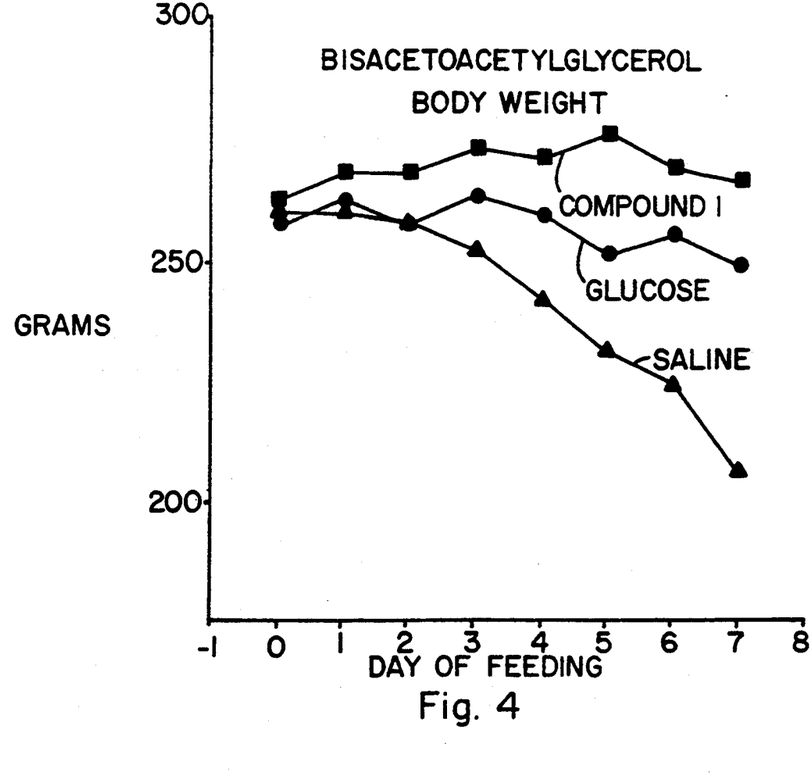
FIG. 4 shows the change in body weight in grams for three groups of rats that were infused with Compound #1, glucose, or saline over a seven day period.

FIG. 4 illustrates the change in body weight during the 7 day treatment of the rats. The individual rat data is listed in table 4. Note that the saline infused rats continually lost weight over 7 days while the other two groups had body weight changes which were consistent with nitrogen balance data.

Table 5 shows the liver weight for individual rats and for each group, and the liver data is presented both as actual liver weight and as a percentage of body weight.

Note that saline infused rats had livers which were smaller in size and a smaller percentage of body weight than did the other two groups. Starvation and semi-starvation both cause a reduction in absolute liver weight and also as a percentage of total body weight. The similarity between glucose infused and experimental compound infused rats liver suggested that the experimental compound was providing significant energy beyond that which was available from oral dietary intake. In addition, table 5 gives the free fatty acid, glucose and ketone body concentrations for the three groups. Free fatty acids were not different for the three groups. Glucose was higher for glucose infused rats than for the other two groups. Rats infused with Compound 1 had normal blood glucose while the saline group had low blood glucose. Total ketone bodies were elevated for rats infused with Compound 1 and the concentration was similar to what has been obtained in other experiments infusing 17% solutions of the monoglyceride (monoacetoacetin).

The rats fed the experimental Compound 1 exhibited better growth and nitrogen retention, and they did not have the hyperglycemia associated with glucose infusion. The concentration of ketonemia was approximately the maximum associated with total fasting in the rat. There is every reason to believe that the diglyceride of acetoacetate would make a good nutrient for parenteral nutrition and that the results would be much improved if the compound were added to a complete parenteral diet.

Example 3: Preparation of 1-acetoacetamido-2,3-propane diol Compound 2

Diketene (555 ml, 7.30 mole) was slowly added to a solution of 1-amino-2,3-propane diol (Aldrich lot no. 15F3513, 666 g, 7.31 mole) in water (1360 g). Throughout the course of the diketene addition (1.5 hours), the reaction temperature was monitored and maintained between 25° and 35° C. through the judicious use of a dry-ice/ethyl acetate cooling bath. The resulting light yellow reaction mixture was left to stir at room temperature for approximately 44 hours before concentration in vacuo. Proton NMR of the crude reaction mixture suggested the presence of a single product in high purity (1.263 kg, 99% of theory). This crude reaction product was crystallized from a heated (to 65° C.) solution of absolute ethanol (1 L) and ethyl acetate (4 L). The resulting crystals which formed on cooling (25° C., overnight) were isolated and dried by suction filtration (1002.7 g, 5.72 mole, 78%). A portion of these crystals (754 g) was again recrystallized from hot ethanol (285 g)/ethyl acetate (2.5 L). The resulting crystals were filtered, washed with 13 wt % of ethanol in ethyl acetate (25° C., 1.1 L) and suction dried (673.47 g, 89% weight recovery, 70% overall yield).

$^1$H NMR (DMSO, digital resolution=0.14 Hz, TMS at half height=0.45 Hz): (keto/enol ratio 92/8) keto form: 8.03 (NH, broad t, J~5), 4.77 (OH, d, J=4.9), 4.54 (OH, t, J=5.8), 3.6–3.42 (m, 1H), 3.36–3.18 (m, 3H), 3.33 (bs, 2H), 3.06–2.85 (m, 1H), 2.14 (t, J=0.4 Hz at 0.07 Hz digital res, 3H). Enolic acetoacetyl resonances were observed at 14.1 (OH, bs), 7.87 (NH, bt, J~5), 5.02 (CH, bs), and at 1.81 (CH3, d, J=0.53).

$^{13}$C NMR (DMSO, digital resolution=0.129 Hz): keto form: 203.1 (S and apparent hextet, J=6.2), 166.3 (Sm), 70.2 (Tm, J=142), 63.5 (Dm, J=137), 51.1 (Tq, J=129.0, 1.5), 42.1 (Tm, J=135.5), 29.9 (Qt, J=127.5, 0.9). Enolic acetoacetyl resonances were also observed at 171.6, 170.8, 91.0 and 20.8.

mp.=70°–71° C.

IR: 3292(br), 1711, 1637, 1561, 1332, 1114, 1096, 1056

FDMS: M=175

Elemental analysis: Calc. for $C_7H_{13}NO_4$: C, 47.99; H, 7.48; N, 8.00 Found: C, 47.67; H, 7.71; N, 7.86

Example 4: Evaluation of 1-acetoacetamido-2,3-propanediol (Compound 2) as a Parenteral Nutrient This compound has an estimated energy density of 4.86 kcal/gram based on thermodynamic data from similar compounds. It was tested for use as a parenteral nutrient in rats as described in Example 2.

Results

A total of 30 rats were started on intravenous infusion and 3 were lost due to various complications. One rat died prior to beginning the infusion on day 0. One rat on the experimental compound was sacrificed because of leaking under the skin which could not be corrected. One rat being infused with saline died from causes unknown. The final rat count was 9 rats infused with experimental compound, 9 rats infused with glucose, and 9 rats infused with saline. The final data are averages from these numbers.

Figure 5:
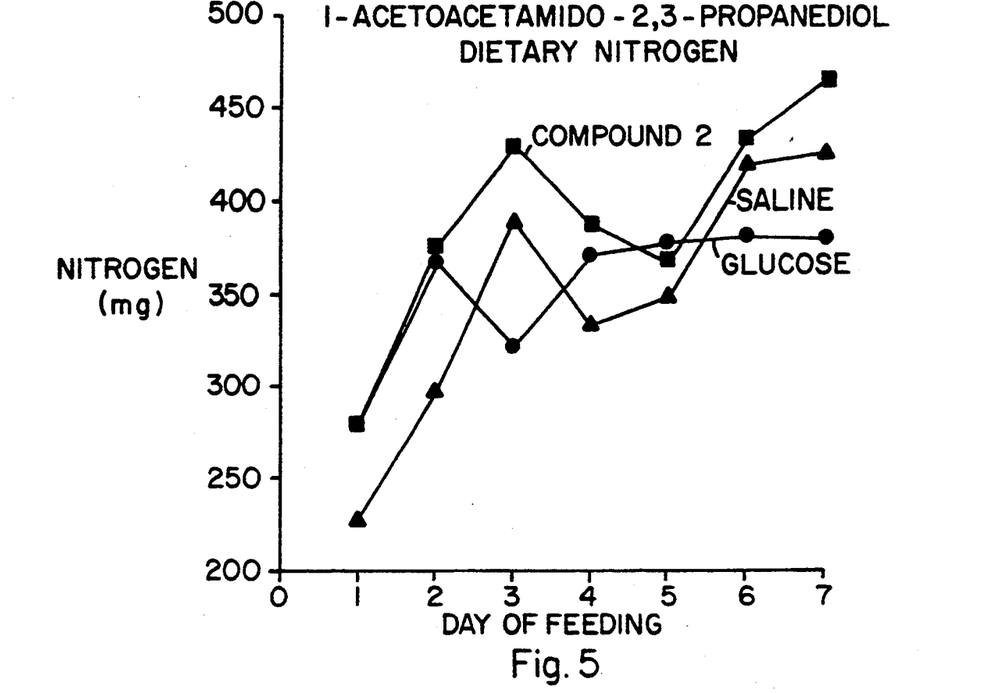
FIG. 5 shows the dietary nitrogen intake in milligrams for three groups of rats that were infused with Compound #2 (1-acetoacetamido-2,3-propanediol), glucose, or saline over a seven day period.

Dietary nitrogen intake for individual rats is listed in table 7 and summarized for each group in FIG. 5. All rats were offered similar amounts of oral dietary nitrogen with the rats infused with the experimental compound fed ad libitum. Other rats were offered amounts similar to that eaten by the rats infused with the experimental compound. FIG. 1 shows that there were no differences in dietary nitrogen intake among the three groups.

It should be stressed that the data in table 7 and in FIG. 5 reflect only oral nitrogen intake. The experimental compound contains 8% nitrogen. With an infusion of 5.6 grams/day, infused nitrogen would provide approximately 450 mg more than that listed in the data tables. The final balance figures includes this number which is calculated based on the actual daily infusion rate for each rat.

One feature to note is the large amount of dietary nitrogen eaten by the experimental rats. Usually, experimental rats have reduced food intake because of the energy provided by the infusion. In this investigation, the experimental rats ate more of the diet than previously seen. The glucose infused rats were not always able to eat the total amount of food offered. Oral non-protein energy intake is a rough estimate of the energy value of the infusate. These data suggest that glucose induced better appetite depression than did the experimental compound. The data also suggested that the experimental compound did not depress the rats appetite.

Figure 6:
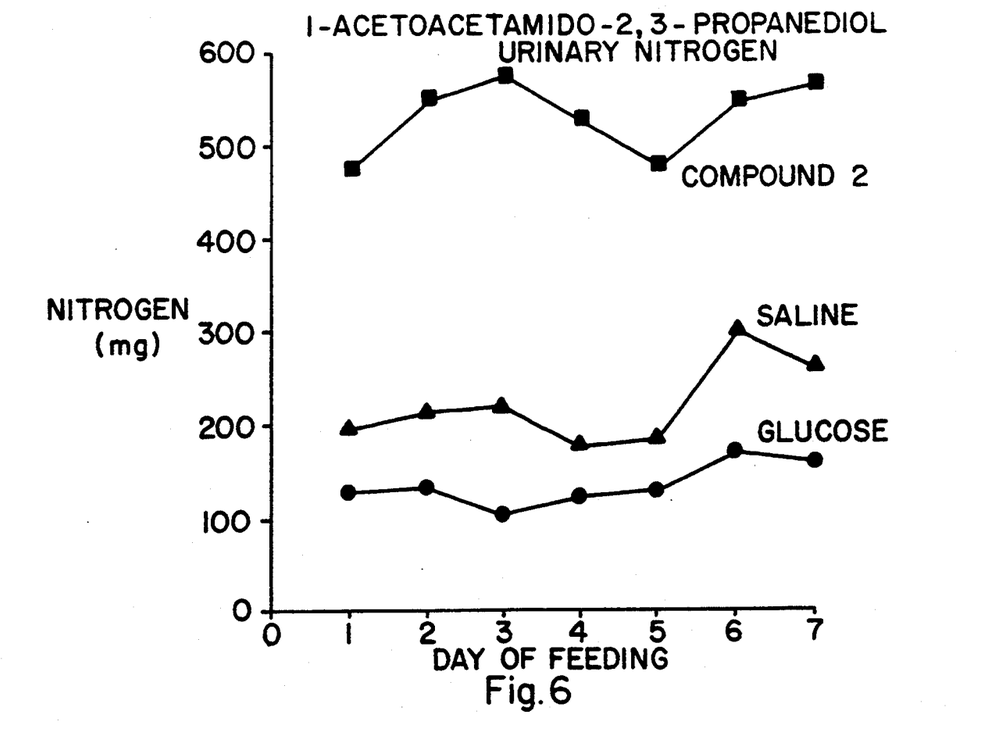
FIG. 6 shows the daily urinary nitrogen losses in milligrams for three groups of rats that were infused with Compound #2, glucose, or saline over a seven day period.

Table 8 lists the individual rat urinary nitrogen losses on a daily basis and FIG. 6 illustrates the daily urinary nitrogen losses for each treatment group over 7 days of treatment. The urinary nitrogen loss pattern is quite different from the dietary nitrogen intake data and reflects the greater nitrogen intake by rats infused with the experimental compound. Saline infused rats also lost more nitrogen in the urine than did glucose infused rats.

Figure 7:
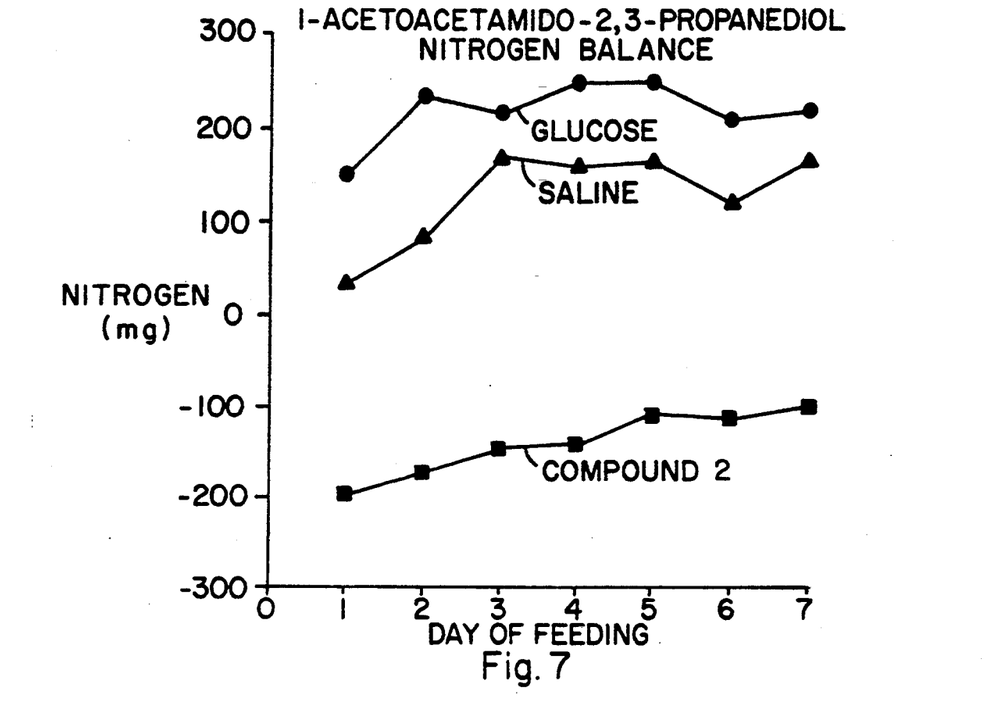
FIG. 7 shows the difference between dietary nitrogen intake and urinary nitrogen output in milligrams (not taking into account infused nitrogen), which is nitrogen balance, for three groups of rats that were infused with Compound #2, glucose, or saline over a seven day period.
Figure 8:
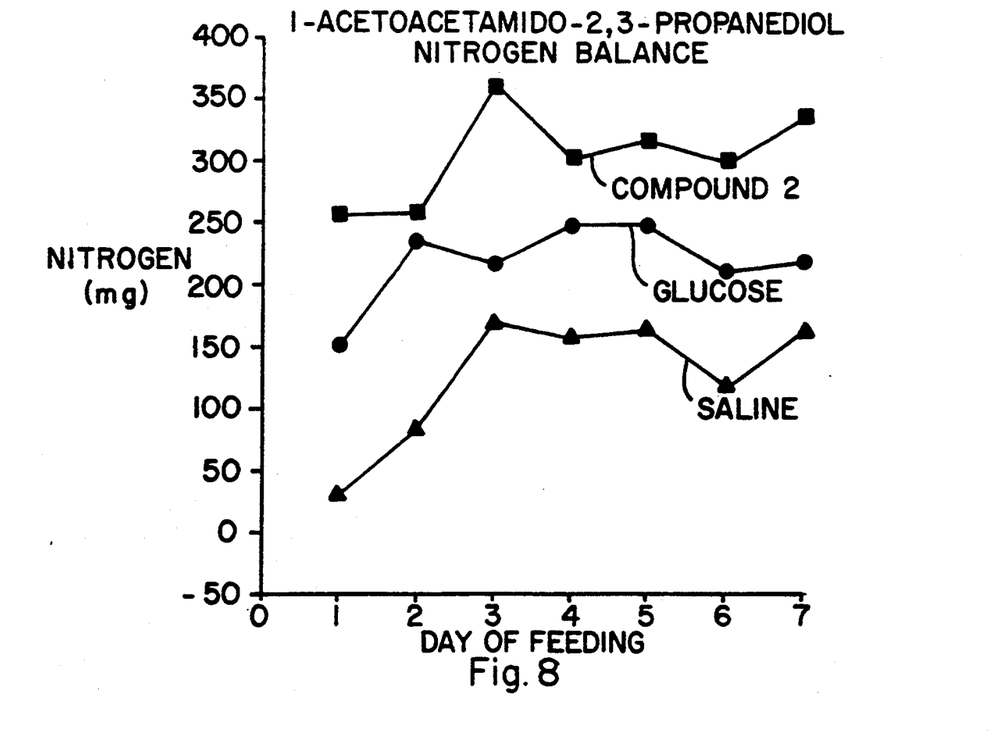
FIG. 8 shows the difference between dietary nitrogen intake (including infused nitrogen) and urinary nitrogen output in milligrams, which is nitrogen balance, for three groups of rats that were infused with Compound #2, glucose, or saline over a seven day period.

FIG. 7 illustrates the difference between oral intake and urinary nitrogen output which is termed nitrogen balance. It is representative of nitrogen balance because urinary nitrogen is the major route for body loss of nitrogen. Data for individual rats is listed in table 9. Rats infused with the experimental compound had a negative nitrogen balance if nitrogen content of the compound is not considered. FIG. 8 shows the nitrogen balance if the infused nitrogen is considered. Both glucose and saline infused rats had positive nitrogen balances with glucose infused rats over 200 mg/day and saline infused rats nearly 150 mg/day. Previous work on monoacetoacetin has indicated that between 100 and 150 mg Nitrogen/day retention is needed to demonstrate gain in body weight.

Figure 9:
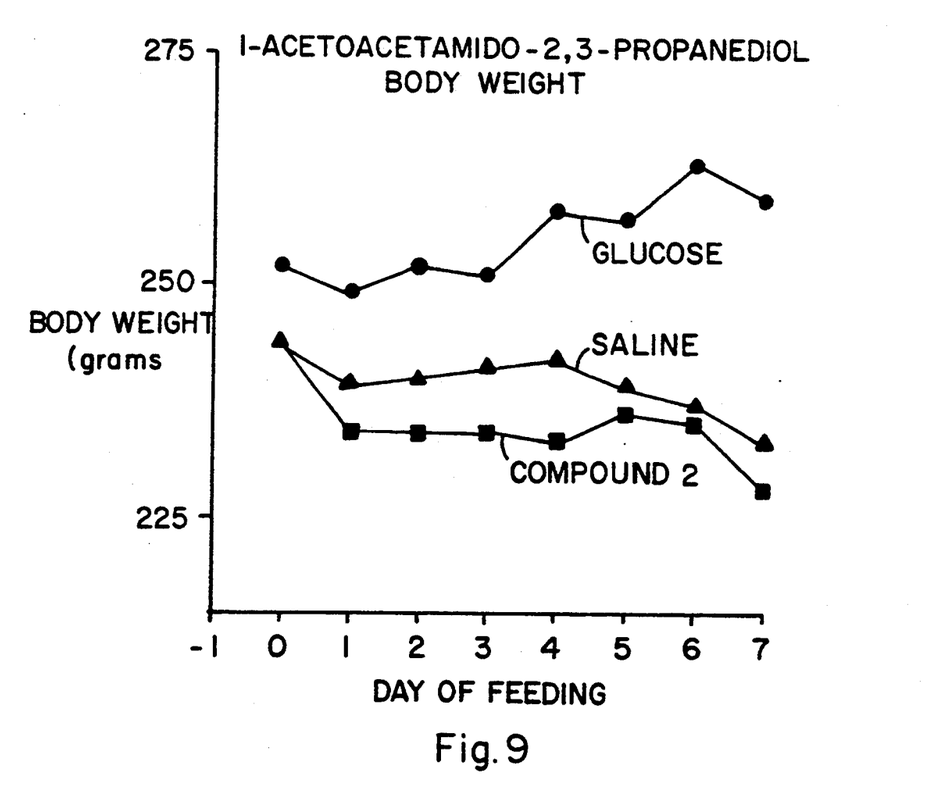
FIG. 9 shows the change in body weight in grams for three groups of rats that were infused with Compound #2, glucose, or saline over a seven day period.

FIG. 9 illustrates the change in body weight during the 7 day treatment of the rats. The individual rat data is listed in table 10. Glucose infused rats did indeed gain weight as suggested by the nitrogen balance data. Saline infused rats did not. They held constant until day 4, and then exhibited a decline in body weight. Rats infused with the experimental compound held relatively constant until the final day when they lose weight.

Table 11 shows the individual and group average values for actual liver weight, liver weight as percentage of body weight, and plasma concentrations of glucose, ketone bodies, and free fatty acids. The liver weights and percentage liver weights were similar for each treatment group suggesting that starvation did not play a role in this study. Glucose infused rats had significantly elevated plasma glucose while experimental compound infused rats had low blood glucose. Saline infused had the usual level. An interesting finding in this data was the absence of elevated plasma acetoacetate in the rats infused with the experimental compound. In fact, neither of the ketone bodies were elevated when compared to the saline infused rats.

Conclusions

It appears that this compound is not a good source of energy. The only clearly defined finding about this compound is that it is not acutely nor chronically lethal.

In summary, rats infused with experimental Compound 2 did not lose weight nor did they gain. The change in their body weight was similar to that of rats infused with saline.

Example 5: Preparation of Pentaacetoacetyl-glucose (Compound 3a)

Pentaacetoacetyl-glucose was prepared by the published method of Elam et. al. (U.S. Pat. No. 4,551,523).

A partial charge of alpha-D-glucose (495 g, 2.75 mole) was added to a stirred solution of distilled 2,2,6-trimethyl-4H-1,3-dioxinone (3.414 kg, 23.73 mole) at 50° C. The resulting heterogeneous solution was brought to 110° C. and the remainder of the alpha-D-glucose was added (360 g, 2.00 mole). The reaction mixture was heated between 90° and 110° C. for 3 hours and 15 minutes with continuous removal of acetone through a distillation take-off head. During the course of the reaction, the solution became homogeneous. Heating was discontinued and the reaction was allowed to cool to room temperature overnight. Proton NMR analysis revealed the presence of pentaacetoacetyl-glucose and traces of acetone, dehydroacetic acid and 2,2,6-trimethyl-4H-1,3-dioxinone. A portion (1898) of the crude reaction product (2.839 kg, 99.6%) was purified (in 200–250 g portions) by dissolving in warm (75°–80° C.) absolute ethanol (88–90 wt % ethanol). Upon cooling to room temperature, the product precipitated as an oil. The resulting oil was swirled at 80° C. for 5 minutes in the presence of absolute ethanol (800 g). Upon cooling to room temperature, the product was isolated by decantation of the ethanol phase. The product (1.37 kg) was dried under vacuum (2 mm Hg) overnight. The ethanol precipitation removed all traces of dehydroacetic acid and 2,2,6-trimethyl-4H-1,3-dioxinone. The major and only discernable product was pentaacetoacetyl-glucose as evidenced both from NMR integration (5 acetoacetyls) but also the resolution of 5 different (non-enolic) acetoacetyl methyl group resonances in the Proton NMR. Careful analysis of the anomeric proton resonances in the proton NMR showed the presence of roughly 78% of pentaacetoacetyl-alpha-D-glucose and 22% of pentaacetoacetyl-beta-D-glucose. The proton NMR could not be further quantitated due to the presence of many minor resonances due to the many possible enolic acetoacetates.

$^1$H NMR (CDCl$_3$): (keto/enol ratio 91/9) keto form: 6.45–6.3 (m, 0.8H-proton on alpha anomeric carbon), 5.8–5.75 (m, 0.2H-proton on beta anomeric carbon), 5.65–5.5 (m, 1H), 5.3–5.05 (m, 2H), 4.45–4.05 (m, 3H), 3.7–3.35 (m, 10H), 2.35–2.20 (m, 15H).

Identifiable enolic resonances: 5.0–4.9 (m, CH), 2.05–1.95 (CH$_3$).

FABMS: M=600 (observed M+potassium=639 in positive mode)

Example 6: The Preparation of Partially Reduced Pentaacetoacetyl-glucose (Compound 3)

Raney Nickel (25 g, W-2 grade, methanol wet) was added to a solution of pentaacetoacetyl glucose from Example 5 (392.6 g, 0.654 mol) in ethylacetate (520.4 g). The resulting mixture was added to a high pressure vessel and magnetically stirred for eight hours under an atmosphere of 3000 psi hydrogen. The reaction vessel was then depressurized, flushed with nitrogen and the contents removed (10% reduction by NMR). An additional charge of raney nickel (25 g) was added to the reaction mixture and the mixture was reintroduced into the high pressure vessel. The contents of the high pressure vessel were stirred at 3,000 psi hydrogen pressure for an additional 24 hours. The reaction vessel was depressurized, flushed with nitrogen and the contents were again removed. Proton NMR analysis indicated approximately 41% reduction in the intensity of acetoacetyl peaks (methyl groups). The resulting material was found to be completely miscible with water at all concentrations.

A second sample of pentaacetoacetyl-glucose (393.4 g) was reduced as above until a 31% reduction in acetoacetyl proton NMR resonances was achieved.

The two reduced samples were combined, filtered through celite, and concentrated in vacuo overnight. The resulting material (708.88 g) was dissolved in distilled, Millipore filtered water (2 L) and passed through a 90 mm (ID) glass column containing a mixed bed ion exchange resin (450 g, Bio-Rad AG-501X8(D)). (No effort was made to recover additional material by rinsing the column bed.) The eluate was concentrated to constant weight (597.6 g) on a freeze dryer (<0.1 mm Hg) over the weekend. Proton NMR of this material indicated between 35 and 38% of the acetoacetates were in reduced form (as hydroxybutyrates).

$^1$H NMR(CDCl$_3$): 6.5–6.25 (m, 0.8H-proton on alpha anomeric carbon), 5.8–5.7 (m, 0.2H-proton on beta anomeric carbon), 5.7–4.7 (m, ca. 3H), 4.6–4.0 (m, ca. 4.75H), 3.7–3.4 (m, ca. 6H), 3.2–2.8 (bs, OH), 2.7–2.33 (m, 3.5H), 2.33–2.1 (m, ca. 8.25H, non-enolic acetoacetate CH3), 2.1-1.8 (m, ca. 1.05H, enolic acetoacetate CH3), 1.35-1.05 (m, ca. 5.7H, hydroxybutyryl CH3).

Metal analysis: Na<10 pppm, Ni<10 ppm, Fe<10 ppm, Al, 19 ppm.

Karl Fisher: Water=1.0%

Elemental analysis: Calc. for $C_{26}H_{35.5}O_{16}$ (35% reduction): C,51.7; H,5.92 Calc. for $C_{26}H_{35.5}O_{16}$ containing 3% water: C,50.1, H,6.08 Found: C,50.05; H,6.13

Negative FABMS: M=602,604,606 (one, two and three reduced acetoacetates) (additional fragmentation peaks also observed which is characteristic for FABMS)

Example 7: Evaluation of Partially Reduced Pentaacetoacetyl-glucose (Compound 3)

The energy density for this compound was estimated to be 3.99 kcal/gram based on thermodynamic data from the individual components. This compound was infused at a rate of 6.77 grams per day to provide 27 kcal/day for each rat. A 13.5% solution was prepared in 0.9% saline solution to ensure that the solution was not hypoosmolar to blood. The rate of infusion would provide 0.06 moles of ketone bodies when fully released which is comparable to the ketone body load provided in previous monoacetoacetin infusion work. The ketone body load is approximately 0.05 moles.

This compound was tested for use as a parenteral nutrient in rats as described in Example 2.

Protocol

Fifteen rats were prepared for intravenous infusion and 5 rats were begun on the experimental compound. All 5 rats were dead within 24 hrs and probably died very early in the infusion as indicated by the lack of urinary output. Visible skin, feet and tail, of the rat were a bright red with the red color being subcutaneous. This suggested diffuse hemolysis of red blood cells with release of the homoglobin into the body water spaces.

After the death of the first five rats, five more rats were infused at 25 ml/day or half the initial rate. These rats also died. Two rats survived for 48 hrs because their pumping systems were leaking. These two rats had elevated blood sugar as indicated by the presence of glucose in the urine. It is not clear how much of the compound these two rats received during the first 24 hrs when the pumps and lines were leaking.

In conclusion, compound 3 was acutely lethal and toxic.

TABLE 1

Dietary Nitrogen Intake In MG N

| RAT NUMBER | PAIR-FED CONTROL: 0.9% NaCl DAY | | | | | | |
|---|---|---|---|---|---|---|---|
| | 0 | 1 | 2 | 3 | 4 | 5 | 6 | 7 |
| 1 | 111.86 | 348.74 | 309.26 | 611.94 | 486.92 | 519.82 | 565.88 |
| 2 | 151.34 | 460.6 | 638.26 | 658 | 559.3 | 217.14 | 263.2 |
| 3 | 131.6 | 184.24 | 138.18 | 118.44 | 210.56 | 105.28 | 184.24 |
| 4 | 138.18 | 144.76 | 276.36 | 414.54 | 250.04 | 309.26 | 197.4 |
| 5 | 473.76 | 506.66 | 421.12 | 585.62 | 342.16 | 381.64 | 440.86 |
| 6 | 177.66 | 348.74 | 447.44 | 427.7 | 256.62 | 434.28 | 493.5 |
| 7 | 125.02 | 98.7 | 171.08 | 125.02 | 223.72 | 131.6 | 177.66 |
| AVERAGE | 187 | 299 | 343 | 420 | 333 | 300 | 332 |
| S.E.M. | 48 | 60 | 66 | 84 | 52 | 59 | 62 |
| BISACETOACETYLGLYCEROL | | | | | | | |
| 8 | 118.44 | 342.16 | 302.68 | 671.16 | 559.3 | 539.56 | 565.88 |
| 9 | 125.02 | 434.28 | 631.68 | 638.26 | 572.46 | 230.3 | 263.2 |
| 10 | 138.18 | 131.6 | 105.28 | 78.96 | 230.3 | 59.22 | 151.34 |
| 11 | 611.94 | 519.82 | 447.44 | 579.04 | 388.22 | 375.06 | 421.12 |
| 12 | 250.04 | 447.44 | 631.68 | 414.54 | 618.52 | 625.1 | 644.84 |
| 13 | 151.34 | 322.42 | 473.76 | 407.96 | 269.78 | 414.54 | 473.76 |
| 14 | 118.44 | 131.6 | 263.2 | 388.22 | 296.1 | 282.94 | 203.98 |
| AVERAGE | 216 | 333 | 408 | 454 | 419 | 361 | 389 |
| S.E.M. | 68 | 58 | 74 | 76 | 61 | 72 | 71 |
| GLUCOSE INFUSED | | | | | | | |
| 15 | 111.86 | 217.14 | 151.34 | 131.6 | 236.88 | 118.44 | 177.66 |
| 16 | 164.5 | 85.54 | 118.44 | 118.44 | 230.3 | 105.28 | 157.92 |
| 17 | 164.5 | 427.7 | 559.3 | 572.46 | 407.96 | 243.46 | 269.78 |
| 18 | 111.86 | 217.14 | 52.64 | 98.7 | 157.92 | 342.16 | 526.4 |
| 19 | 111.86 | 144.76 | 250.04 | 394.8 | 223.72 | 289.52 | 210.56 |
| 20 | 486.92 | 493.5 | 276.36 | 414.54 | 217.14 | 375.06 | 473.76 |
| 21 | 269.78 | 526.4 | 631.68 | 526.4 | 559.3 | 644.84 | 664.58 |
| AVERAGE | 203 | 302 | 291 | 322 | 290 | 303 | 354 |
| S.E.M. | 52 | 67 | 84 | 77 | 53 | 69 | 75 |

TABLE 2

Urinary Nitrogen In MG

| RAT NUMBER | PAIR-FED CONTROL: 0.9% NaCl DAY | | | | | | |
|---|---|---|---|---|---|---|---|
| | 0 | 1 | 2 | 3 | 4 | 5 | 6 | 7 |
| 1 | | 365.43 | 352.4 | 428.58 | 554.12 | 376.19 | 519.18 | 256.87 |
| 2 | | 307.52 | 400.47 | 299.77 | 481.2 | 410.9 | 216.02 | 326.67 |
| 3 | | 159.99 | 130.54 | 106.29 | 173.95 | 275.73 | 318.78 | 368.64 |
| 4 | | 31.59 | 140.67 | 262.83 | 271.85 | 111.89 | 327.55 | 284.93 |
| 5 | | 208.94 | 295.56 | 226.74 | 248.41 | 186.84 | 276.59 | 22.47 |
| 6 | | 102.69 | 290.84 | 167.77 | 339.77 | 305.87 | 300.25 | 229.44 |
| 7 | | 114.89 | 101.55 | 116.47 | 173.72 | 271.99 | 464.82 | 291.27 |
| AVERAGE | | 184 | 245 | 230 | 320 | 277 | 346 | 254 |
| S.E.M. | | 45 | 45 | 43 | 56 | 39 | 41 | 42 |

TABLE 2-continued

Urinary Nitrogen In MG

PAIR-FED CONTROL: 0.9% NaCl

| RAT NUMBER | 0 | 1 | 2 | 3 | 4 | 5 | 6 | 7 |
|---|---|---|---|---|---|---|---|---|
| BISACETOACETYLGLYCEROL | | | | | | | | |
| 8 | | 116.21 | 315.78 | 181.94 | 294.68 | 289.81 | 283.02 | 381.14 |
| 9 | | 250.2 | 264.22 | 142.42 | 253.62 | 303.16 | 191.83 | 194.98 |
| 10 | | 187.3 | 139.27 | 62.97 | 47.06 | 254.66 | 11.17 | 152.92 |
| 11 | | 123.37 | 174.34 | 164.52 | 193.72 | 144.16 | 134.85 | 192.67 |
| 12 | | 182.18 | 187.22 | 162.29 | 139.67 | 274.72 | 378.79 | 269.64 |
| 13 | | 159.89 | 165.19 | 140.13 | 115.59 | 97.81 | 184.37 | 203.37 |
| 14 | | 145.06 | 94.71 | 104.72 | 168.33 | 142.32 | 179.01 | 138.8 |
| AVERAGE | | 166 | 192 | 137 | 173 | 215 | 195 | 219 |
| S.E.M. | | 17 | 28 | 15 | 32 | 32 | 43 | 31 |
| GLUCOSE INFUSED | | | | | | | | |
| 15 | | 164.08 | 131.95 | 58.42 | 109.72 | 111.02 | 114.67 | 71.89 |
| 16 | | 92.04 | 74.58 | 94.88 | 80.52 | 125.89 | 65.54 | 105.54 |
| 17 | | 219.2 | 311.7 | 599.66 | 274.22 | 316.17 | 227.23 | 474.91 |
| 18 | | 80.25 | 147.44 | 115.01 | 93.31 | 84.8 | 135.24 | 159.89 |
| 19 | | 78.51 | 42.51 | 145.05 | 78.6 | 224.34 | 118.95 | 124.66 |
| 20 | | 282.44 | 224.09 | 174.3 | 145.43 | 241.17 | 333.85 | 267 |
| 21 | | 88.28 | 88.37 | 236.92 | 124.12 | 137.97 | 252.42 | 319.39 |
| AVERAGE | | 144 | 146 | 203 | 129 | 177 | 178 | 218 |
| S.E.M. | | 31 | 35 | 70 | 26 | 32 | 36 | 55 |

TABLE 3

Nitrogen Balance In MG N Difference Between Intake and Output

PAIR-FED CONTROL: 0.9% NaCl

| RAT NUMBER | 0 | 1 | 2 | 3 | 4 | 5 | 6 | 7 |
|---|---|---|---|---|---|---|---|---|
| 1 | | −253.57 | −3.66 | −119.32 | 57.82 | 110.73 | 0.64 | 309.01 |
| 2 | | −156.18 | 60.13 | 338.49 | 176.8 | 148.4 | 1.12 | −63.47 |
| 3 | | −28.39 | 53.7 | 31.89 | −55.51 | −65.17 | −213.5 | −184.4 |
| 4 | | 106.59 | 4.09 | 13.53 | 142.69 | 138.15 | −18.29 | −87.53 |
| 5 | | 264.82 | 211.1 | 194.38 | 337.21 | 155.32 | 105.05 | 418.39 |
| 6 | | 74.97 | 57.9 | 279.67 | 87.93 | −49.25 | 134.03 | 264.06 |
| 7 | | 10.13 | −2.85 | 54.61 | −48.7 | −48.27 | −333.22 | −113.61 |
| AVERAGE | | 3 | 54 | 113 | 100 | 56 | −46 | 77 |
| S.E.M. | | 65 | 28 | 62 | 52 | 39 | 64 | 92 |
| BISACETOACETYLGLYCEROL | | | | | | | | |
| 8 | | 2.23 | 26.38 | 120.74 | 376.48 | 269.49 | 256.54 | 184.74 |
| 9 | | −125.18 | 170.06 | 489.26 | 384.64 | 269.3 | 38.47 | 68.22 |
| 10 | | −49.12 | −7.67 | 42.31 | 31.9 | −24.36 | 48.05 | −1.58 |
| 11 | | 488.57 | 345.48 | 282.92 | 385.32 | 244.06 | 240.21 | 228.45 |
| 12 | | 67.86 | 260.22 | 469.39 | 274.87 | 343.8 | 246.31 | 375.2 |
| 13 | | −8.55 | 157.23 | 333.63 | 292.37 | 171.97 | 230.17 | 270.39 |
| 14 | | −26.62 | 36.89 | 158.48 | 219.89 | 153.78 | 103.93 | 65.18 |
| AVERAGE | | 50 | 141 | 271 | 281 | 204 | 166 | 170 |
| S.E.M. | | 76 | 50 | 65 | 48 | 45 | 37 | 50 |
| GLUCOSE INFUSED | | | | | | | | |
| 15 | | −52.22 | 85.19 | 92.92 | 21.88 | 125.86 | 3.77 | 105.77 |
| 16 | | 72.46 | 10.96 | 23.56 | 37.92 | 104.41 | 39.74 | 52.38 |
| 17 | | −54.7 | 116 | −40.36 | 298.24 | 91.79 | 16.23 | −205.13 |
| 18 | | 31.61 | 69.7 | −62.37 | 5.39 | 73.12 | 206.92 | 366.51 |
| 19 | | 33.35 | 102.25 | 104.99 | 316.2 | −0.62 | 170.57 | 85.9 |
| 20 | | 204.48 | 269.41 | 102.06 | 269.11 | −24.03 | 41.21 | 206.76 |
| 21 | | 181.5 | 438.03 | 394.76 | 402.28 | 421.33 | 392.42 | 345.19 |
| AVERAGE | | 59 | 156 | 88 | 193 | 113 | 124 | 137 |
| S.E.M. | | 39 | 56 | 57 | 63 | 55 | 54 | 74 |

TABLE 4

Rats Daily Body Weights in Grams

PAIR-FED CONTROL: 0.9% NaCl

| RAT NUMBER | 0 | 1 | 2 | 3 | 4 | 5 | 6 | 7 |
|---|---|---|---|---|---|---|---|---|
| 1 | 261 | 271 | 275 | 260 | 237 | 216 | 205 | 193 |
| 2 | 298 | 304 | 294 | 288 | 285 | 283 | 273 | 248 |
| 3 | 264 | 258 | 251 | 240 | 230 | 218 | 202 | 185 |
| 4 | 245 | 238 | 239 | 236 | 236 | 210 | 203 | 174 |
| 5 | 280 | 284 | 282 | 286 | 270 | 279 | 282 | 267 |
| 6 | 239 | 246 | 243 | 240 | 243 | 234 | 220 | 220 |
| 7 | 224 | 222 | 218 | 213 | 197 | 182 | 167 | 158 |
| AVERAGE | 259 | 260 | 257 | 252 | 242 | 231 | 224 | 206 |
| S.E.M. | 10 | 11 | 10 | 10 | 11 | 14 | 16 | 15 |
| BISACETOACETYLGLYCEROL | | | | | | | | |
| 8 | 282 | 311 | 273 | 278 | 265 | 261 | 253 | 249 |
| 9 | 278 | 290 | 289 | 286 | 284 | 276 | 261 | 261 |
| 10 | 233 | 230 | 232 | 258 | 226 | 234 | 252 | 253 |
| 11 | 283 | 284 | 297 | 292 | 302 | 306 | 310 | 307 |
| 12 | 268 | 268 | 279 | 278 | 280 | 285 | 281 | 276 |
| 13 | 246 | 249 | 249 | 256 | 262 | 293 | 269 | 273 |
| 14 | 244 | 241 | 256 | 263 | 276 | 277 | 260 | 245 |
| AVERAGE | 262 | 268 | 268 | 273 | 271 | 276 | 269 | 266 |

TABLE 4-continued

Rats Daily Body Weights in Grams

PAIR-FED CONTROL: 0.9% NaCl

| RAT NUMBER | DAY 0 | 1 | 2 | 3 | 4 | 5 | 6 | 7 |
|---|---|---|---|---|---|---|---|---|
| S.E.M. | 8 | 11 | 9 | 5 | 9 | 9 | 8 | 8 |
| GLUCOSE INFUSED | | | | | | | | |
| 15 | 244 | 238 | 234 | 229 | 232 | 232 | 257 | 245 |
| 16 | 228 | 217 | 211 | 209 | 207 | 212 | 230 | 228 |
| 17 | 290 | 329 | 298 | 337 | 315 | 278 | 274 | 251 |
| 18 | 250 | 236 | 233 | 231 | 226 | 222 | 220 | 226 |
| 19 | 247 | 244 | 248 | 266 | 246 | 240 | 238 | 230 |
| 20 | 281 | 286 | 293 | 282 | 295 | 279 | 274 | 268 |
| 21 | 269 | 284 | 281 | 286 | 291 | 294 | 293 | 297 |
| AVERAGE | 258 | 262 | 257 | 263 | 259 | 251 | 255 | 249 |
| S.E.M. | 8 | 15 | 13 | 17 | 16 | 12 | 10 | 10 |

TABLE 5

Saline

| Rat Number | Grams Liver Wt. | Liver/ 100 GM | mMOL/L FFa | mg/dl Glucose | mMOL/L ACAC | mMOL/L BOHB | T.KB | Ratio: A/B |
|---|---|---|---|---|---|---|---|---|
| 1 | 6.63 | 3.435 | 0.864 | 116.540 | 0.154 | 0.609 | 0.763 | 3.955 |
| 2 | 6.21 | 2.504 | 0.555 | 130.500 | 0.061 | 0.464 | 0.525 | 7.607 |
| 3 | 3.04 | 1.643 | 0.049 | 46.460 | 0.078 | 0.081 | 0.159 | 1.029 |
| 4 | 3.31 | 1.902 | 0.182 | 125.200 | 0.189 | 0.264 | 0.453 | 1.395 |
| 5 | 5.83 | 2.184 | 0.414 | 114.300 | 0.238 | 0.739 | 0.977 | 3.106 |
| 6 | 6.12 | 2.782 | 0.574 | 73.800 | 0.449 | 1.668 | 2.118 | 3.712 |
| 7 | 2.82 | 1.785 | 0.569 | 12.200 | 0.032 | 0.079 | 0.110 | 2.483 |
| AVERAGE | 4.851 | 2.319 | 0.458 | 88.429 | 0.172 | 0.558 | 0.729 | 3.327 |
| S.E.M. | 0.643 | 0.240 | 0.103 | 17.160 | 0.054 | 0.208 | 0.259 | 0.826 |
| Compound # | | | | | | | | |
| 8 | 7.12 | 2.859 | 0.540 | 94.920 | 0.982 | 0.797 | 1.779 | 0.812 |
| 9 | 9.12 | 3.494 | 0.574 | 149.000 | 0.851 | 0.770 | 1.621 | 0.905 |
| 10 | 7.92 | 3.130 | 0.745 | 114.200 | 0.939 | 1.059 | 1.998 | 1.128 |
| 11 | 11.65 | 3.795 | 0.466 | 163.500 | 0.447 | 0.529 | 0.976 | 1.185 |
| 12 | 6.85 | 2.482 | 0.483 | 89.000 | 0.869 | 1.021 | 1.890 | 1.175 |
| 13 | 8.69 | 3.183 | 0.615 | 122.100 | 0.550 | 0.404 | 0.954 | 0.735 |
| 14 | 8.87 | 3.620 | 0.519 | 91.800 | 0.377 | 0.849 | 1.226 | 2.254 |
| AVERAGE | 8.603 | 3.223 | 0.563 | 117.789 | 0.716 | 0.776 | 1.492 | 1.171 |
| S.E.M. | 0.605 | 0.173 | 0.036 | 11.044 | 0.095 | 0.091 | 0.165 | 0.193 |
| Glucose | | | | | | | | |
| 15 | 6.37 | 2.600 | 0.337 | 196.840 | 0.020 | 0.385 | 0.405 | 19.250 |
| 16 | 7.6 | 3.333 | 0.976 | 161.300 | 0.066 | 0.476 | 0.542 | 7.212 |
| 17 | 8.17 | 3.255 | 0.850 | 162.620 | 0.194 | 0.533 | 0.727 | 2.748 |
| 18 | 9.51 | 4.208 | 0.816 | 164.800 | 0.096 | 0.332 | 0.427 | 3.466 |
| 19 | 7.03 | 3.057 | 0.168 | 237.100 | 0.017 | 0.358 | 0.375 | 21.178 |
| 20 | 8.05 | 3.004 | 0.483 | 228.500 | 0.194 | 1.086 | 1.280 | 5.600 |
| 21 | 9.15 | 3.081 | 0.316 | 146.800 | 0.031 | 0.363 | 0.394 | 11.557 |
| AVERAGE | 7.983 | 3.220 | 0.564 | 185.423 | 0.088 | 0.505 | 0.593 | 10.144 |
| S.E.M. | 0.419 | 0.187 | 0.119 | 13.518 | 0.029 | 0.101 | 0.124 | 2.825 |

TABLE 6

ENERGY DENSITY CALCULATION FOR MIXTURE OF COMPOUNDS AS #1

| | | | |
|---|---|---|---|
| 1,3-ISOMER | 132 | | |
| | 112 | | |
| | 16 | MOLE % | KCAL/GM |
| | M.W. = 260 | 58 | 4.33 |
| 1,2-ISOMER | 132 | | |
| | 112 | | |
| | 16 | MOLE % | KCAL/GM |
| | M.W. = 260 | 22 | 4.33 |
| 1,2,3 ISOMER | 180 | | |
| | 144 | | |
| | 20 | MOLE % | |
| | M.W. = 344 | 14 | 4.33 |
| 1 ISOMER | 84 | | |
| | 80 | | |
| | 12 | MOLE % | |
| | M.W. = 176 | 6 | 4.32 |

MOLE % IS APPROXIMATE

TABLE 7

Dietary Nitrogen Intake In MG N

PAIR-FED CONTROL: 0.9% NaCl

| RAT NUMBER | DAY 1 | 2 | 3 | 4 | 5 | 6 | 7 |
|---|---|---|---|---|---|---|---|
| 1 | 184.24 | 32.9 | 401.38 | 447.44 | 467.18 | 513.24 | 427.7 |
| 2 | 105.28 | 276.36 | 407.96 | 250.04 | 427.7 | 361.9 | 434.28 |
| 3 | 138.18 | 105.28 | 144.76 | 65.8 | 0 | 0 | 72.38 |
| 4 | 302.68 | 315.84 | 407.96 | 190.82 | 329 | 388.22 | 480.34 |
| 5 | 302.68 | 486.92 | 500.08 | 486.92 | 460.6 | 480.34 | 421.12 |
| 6 | 111.86 | 276.36 | 486.92 | 276.36 | 39.48 | 519.82 | 500.08 |
| 7 | 407.96 | 440.86 | 500.08 | 473.76 | 480.34 | 500.08 | 486.92 |
| 8 | 355.32 | 473.76 | 473.76 | 486.92 | 473.76 | 513.24 | 500.08 |
| 9 | 131.6 | 263.2 | 190.82 | 329 | 460.6 | 506.66 | 506.66 |
| AVERAGE | 227 | 297 | 390 | 334 | 349 | 420 | 426 |
| S.E.M. | 39 | 52 | 44 | 50 | 64 | 56 | 46 |
| 1-Acetoacetamido-2,3-propanediol | | | | | | | |
| 10 | 513.24 | 532.98 | 532.98 | 480.34 | 480.34 | 526.4 | 526.4 |
| 11 | 92.12 | 256.62 | 407.96 | 263.2 | 427.7 | 421.12 | 546.14 |
| 12 | 164.5 | 526.4 | 546.14 | 473.76 | 355.32 | 388.22 | 506.66 |

TABLE 7-continued

Dietary Nitrogen Intake In MG N
PAIR-FED CONTROL: 0.9% NaCl

| RAT NUMBER | 0 | 1 | 2 | 3 | 4 | 5 | 6 | 7 |
|---|---|---|---|---|---|---|---|---|
| 13 | | 138.18 | 59.22 | 118.44 | 65.8 | 0 | 0 | 0 |
| 14 | | 171.08 | 282.94 | 506.66 | 296.1 | 52.64 | 519.82 | 506.66 |
| 15 | | 493.5 | 506.66 | 500.08 | 519.82 | 500.08 | 526.4 | 506.66 |
| 16 | | 138.18 | 263.2 | 210.56 | 355.32 | 480.34 | 500.08 | 532.98 |
| 17 | | 440.86 | 447.44 | 513.24 | 519.82 | 519.82 | 513.24 | 546.14 |
| 18 | | 355.32 | 506.66 | 526.4 | 519.82 | 506.66 | 506.66 | 519.82 |
| AVERAGE | | 279 | 376 | 429 | 388 | 369 | 434 | 466 |
| S.E.M. | | 57 | 56 | 52 | 52 | 67 | 57 | 58 |
| Glucose Infused | | | | | | | | |
| 19 | | 500.08 | 519.82 | 355.32 | 401.38 | 421.12 | 454.02 | 421.12 |
| 20 | | 388.22 | 513.24 | 388.22 | 342.16 | 368.48 | 375.06 | 414.54 |
| 21 | | 164.5 | 500.08 | 394.8 | 427.7 | 335.58 | 329 | 355.32 |
| 22 | | 151.34 | 98.7 | 151.34 | 85.54 | 0 | 0 | 32.9 |
| 23 | | 78.96 | 269.78 | 394.8 | 282.94 | 421.12 | 394.8 | 401.38 |
| 24 | | 421.12 | 434.28 | 467.18 | 480.34 | 427.7 | 421.12 | 473.76 |
| 25 | | 329 | 342.16 | 407.96 | 486.92 | 454.02 | 447.44 | 407.96 |
| 26 | | 98.7 | 243.46 | 197.4 | 335.58 | 493.5 | 519.82 | 500.08 |
| 27 | | 375.06 | 401.38 | 151.34 | 506.66 | 493.5 | 500.08 | 421.12 |
| AVERAGE | | 279 | 369 | 323 | 372 | 379 | 382 | 381 |
| S.E.M. | | 52 | 48 | 41 | 44 | 50 | 52 | 46 |

TABLE 8

Urinary Nitrogen In MG
PAIR-FED CONTROL: 0.9% NaCl

| RAT NUMBER | 0 | 1 | 2 | 3 | 4 | 5 | 6 | 7 |
|---|---|---|---|---|---|---|---|---|
| 1 | | 239.9 | 190.8 | 277.7 | 246.5 | 217.5 | 233.4 | 162.8 |
| 2 | | 219.2 | 207.2 | 184.3 | 116.9 | 128.7 | 159.4 | 195.8 |
| 3 | | 176.8 | 180.5 | 107.6 | 72.6 | 80 | 145.9 | 158.9 |
| 4 | | 105.6 | 138.7 | 138 | 95.1 | 119.3 | 151 | 247 |
| 5 | | 186.6 | 290.1 | 261.9 | 200.1 | 180.1 | 208.6 | 224.2 |
| 6 | | 145.9 | 145.7 | 244.2 | 139.2 | 108.8 | 334.8 | 335.8 |
| 7 | | 259.9 | 243.8 | 266 | 248.8 | 269.5 | 326.4 | 309.7 |
| 8 | | 205.2 | 280.3 | 290.7 | 232.1 | 234.6 | 294.7 | 291.1 |
| 9 | | 216 | 248 | 218.2 | 239.1 | 333.7 | 873.4 | 439.8 |
| AVERAGE | | 195 | 214 | 221 | 177 | 186 | 303 | 263 |
| S.E.M. | | 16 | 18 | 22 | 24 | 28 | 75 | 30 |
| 1-Acetoacetamido-2,3-propanediol | | | | | | | | |
| 10 | | 562.1 | 661.5 | 671.9 | 559.8 | 599 | 569 | 602 |
| 11 | | 483.2 | 542.5 | 704.1 | 477.4 | 456 | 659.4 | 613.5 |
| 12 | | 380.8 | 499.8 | 548.1 | 468.3 | 434.3 | 440.8 | 519.4 |
| 13 | | 411.4 | 464 | 413.8 | 385 | 300.2 | 286.1 | 81.4 |
| 14 | | 401.7 | 462.84 | 619.3 | 499.7 | 365.9 | 545.2 | 588.3 |
| 15 | | 527.6 | 583.3 | 603.8 | 603.7 | 503.5 | 538.5 | 633.1 |
| 16 | | 477.8 | 486 | 315.2 | 494.3 | 525.1 | 608.2 | 678 |
| 17 | | 509.6 | 528 | 622.2 | 614.8 | 552.9 | 599 | 683.9 |
| 18 | | 536.4 | 718.2 | 682.4 | 674.2 | 572.3 | 686.7 | 706.8 |
| AVERAGE | | 477 | 550 | 576 | 531 | 479 | 548 | 567 |
| S.E.M. | | 22 | 30 | 44 | 30 | 33 | 41 | 64 |
| Glucose Infused | | | | | | | | |
| 19 | | 252 | 266.4 | 151 | 127.2 | 127.8 | 256.3 | 118.3 |
| 20 | | 114.8 | 153.9 | 89.1 | 92.7 | 97.7 | 104.9 | 106.6 |
| 21 | | 82.1 | 105 | 107.2 | 114.8 | 93.7 | 133.7 | 175.8 |
| 22 | | 75.4 | 57 | 68.4 | 44.5 | 45.9 | 72.7 | 22.6 |
| 23 | | 22.4 | 91.8 | 118.3 | 73.8 | 84.8 | 138.3 | 145.6 |
| 24 | | 158.4 | 159.8 | 131.9 | 165.9 | 236.3 | 307.5 | 384.8 |
| 25 | | 133.9 | 111 | 135.4 | 168.7 | 166.4 | 146.9 | 126.8 |
| 26 | | 148.3 | 108.9 | 59.8 | 93.6 | 123.4 | 169.4 | 162.4 |
| 27 | | 164.3 | 158 | 91.8 | 240.1 | 203.2 | 215.2 | 212.8 |
| AVERAGE | | 128 | 135 | 106 | 125 | 131 | 172 | 162 |
| S.E.M. | | 22 | 20 | 10 | 20 | 20 | 25 | 33 |

TABLE 9

Nitrogen Balance In MG W Difference Between Intake And Output
PAIR-FED CONTROL: 0.9% NaCl

| RAT NUMBER | 0 | 1 | 2 | 3 | 4 | 5 | 6 | 7 |
|---|---|---|---|---|---|---|---|---|
| 1 | | −55.66 | −157.9 | 123.68 | 200.94 | 249.68 | 279.84 | 264.9 |
| 2 | | −113.92 | 69.16 | 223.66 | 133.14 | 299 | 202.5 | 238.48 |
| 3 | | −38.62 | −75.22 | 37.16 | −6.8 | −80 | −145.9 | −86.52 |
| 4 | | 197.08 | 177.14 | 269.96 | 95.72 | 209.7 | 237.22 | 233.34 |

TABLE 9-continued

Nitrogen Balance In MG W Difference Between Intake And Output

PAIR-FED CONTROL: 0.9% NaCl

| RAT NUMBER | DAY | | | | | | | |
|---|---|---|---|---|---|---|---|---|
| | 0 | 1 | 2 | 3 | 4 | 5 | 6 | 7 |
| 5 | | 116.08 | 196.82 | 238.18 | 286.82 | 280.5 | 271.74 | 196.92 |
| 6 | | −34.04 | 130.66 | 242.72 | 137.16 | −69.32 | 185.02 | 164.28 |
| 7 | | 148.06 | 197.06 | 234.08 | 224.96 | 210.84 | 173.68 | 177.22 |
| 8 | | 150.12 | 193.46 | 183.06 | 254.82 | 239.16 | 218.54 | 208.98 |
| 9 | | −84.4 | 15.2 | −27.38 | 89.9 | 126.9 | −366.74 | 66.86 |
| AVERAGE | | 32 | 83 | 169 | 157 | 163 | 117 | 163 |
| S.E.M. | | 40 | 44 | 35 | 31 | 48 | 74 | 37 |
| 1-Acetoacetamido-2,3-propanediol | | | | | | | | |
| 10 | | −48.40 | −128.09 | −138.41 | −79.03 | −118.19 | −42.18 | −75.13 |
| 11 | | −390.63 | −285.45 | −295.62 | −213.75 | −27.80 | −237.99 | −66.99 |
| 12 | | −215.89 | 27.00 | −1.50 | 5.85 | −78.58 | −52.22 | −12.35 |
| 13 | | −272.80 | −404.37 | −294.88 | −318.78 | −299.78 | −285.71 | −80.98 |
| 14 | | −230.17 | −179.52 | −112.14 | −203.13 | −312.86 | −24.92 | −81.18 |
| 15 | | −33.64 | −76.20 | −103.23 | −83.45 | −3.03 | −11.68 | −126.00 |
| 16 | | −339.15 | −222.34 | −104.12 | −138.51 | −44.36 | −107.66 | −144.55 |
| 17 | | −68.27 | −80.10 | −108.44 | −94.52 | −32.68 | −85.30 | −137.30 |
| 18 | | −180.58 | −211.06 | −155.44 | −153.89 | −65.20 | −179.57 | −186.50 |
| AVERAGE | | −198 | −173 | −146 | −142 | −109 | −114 | −101 |
| S.E.M. | | 43 | 43 | 32 | 32 | 39 | 33 | 17 |
| Glucose Infused | | | | | | | | |
| 19 | | 248.08 | 253.42 | 204.32 | 274.18 | 293.32 | 197.72 | 306.82 |
| 20 | | 273.42 | 359.34 | 299.12 | 249.46 | 270.78 | 270.16 | 307.94 |
| 21 | | 82.4 | 395.08 | 287.6 | 312.9 | 241.88 | 195.3 | 179.52 |
| 22 | | 75.94 | 41.7 | 82.94 | 41.04 | −45.9 | −72.7 | 10.3 |
| 23 | | 56.56 | 177.98 | 276.5 | 209.14 | 336.32 | 256.5 | 255.78 |
| 24 | | 262.72 | 274.48 | 335.28 | 314.44 | 191.4 | 113.62 | 88.96 |
| 25 | | 195.1 | 231.16 | 272.56 | 318.22 | 287.62 | 300.54 | 281.16 |
| 26 | | −49.6 | 134.56 | 137.6 | 241.98 | 370.1 | 350.42 | 337.68 |
| 27 | | 210.76 | 243.38 | 59.54 | 266.56 | 290.3 | 284.88 | 208.32 |
| AVERAGE | | 151 | 235 | 217 | 248 | 248 | 211 | 219 |
| S.E.M. | | 38 | 36 | 34 | 29 | 41 | 42 | 37 |

TABLE 9A

Nitrogen Balance In MG W Difference Between Intake And Output

PAIR-FED CONTROL: 0.9% NaCl

| RAT NUMBER | DAY | | | | | | | |
|---|---|---|---|---|---|---|---|---|
| | 0 | 1 | 2 | 3 | 4 | 5 | 6 | 7 |
| 1 | | −55.66 | −157.9 | 123.68 | 200.94 | 249.68 | 279.84 | 264.9 |
| 2 | | −113.92 | 69.16 | 223.66 | 133.14 | 299 | 202.5 | 238.48 |
| 3 | | −38.62 | −75.22 | 37.16 | −6.8 | −80 | −145.9 | −86.52 |
| 4 | | 197.08 | 177.14 | 269.96 | 95.72 | 209.7 | 237.22 | 233.34 |
| 5 | | 116.08 | 196.82 | 238.18 | 286.82 | 280.5 | 271.74 | 196.92 |
| 6 | | −34.04 | 130.66 | 242.72 | 137.16 | −69.32 | 185.02 | 164.28 |
| 7 | | 148.06 | 197.06 | 234.08 | 224.96 | 210.84 | 173.68 | 177.22 |
| 8 | | 150.12 | 193.46 | 183.06 | 254.82 | 239.16 | 218.54 | 208.98 |
| 9 | | −84.4 | 15.2 | −27.38 | 89.9 | 126.9 | −366.74 | 66.86 |
| AVERAGE | | 32 | 83 | 169 | 157 | 163 | 117 | 163 |
| S.E.M. | | 40 | 44 | 35 | 31 | 48 | 74 | 37 |
| 1-Acetoacetamido-2,3-propanediol | | | | | | | | |
| 10 | | 408.10 | 301.56 | 371.80 | 350.62 | 347.26 | 378.52 | 390.32 |
| 11 | | 56.92 | 144.20 | 223.54 | 233.80 | 473.46 | 48.44 | 300.00 |
| 12 | | 195.86 | 429.80 | 455.00 | 399.70 | 324.22 | 305.82 | 372.54 |
| 13 | | 147.90 | 7.38 | 188.48 | 101.92 | 120.92 | 99.18 | 339.72 |
| 14 | | 217.38 | 196.42 | 389.12 | 262.32 | 89.94 | 431.58 | 375.32 |
| 15 | | 422.86 | 362.40 | 389.08 | 346.20 | 390.82 | 409.02 | 312.60 |
| 16 | | 135.26 | 234.16 | 415.04 | 326.94 | 358.44 | 348.84 | 320.90 |
| 17 | | 397.18 | 376.40 | 410.72 | 361.98 | 370.12 | 371.20 | 319.20 |
| 18 | | 320.68 | 272.30 | 408.48 | 338.42 | 373.40 | 294.84 | 296.86 |
| AVERAGE | | 256 | 258 | 361 | 302 | 317 | 299 | 336 |
| S.E.M. | | 45 | 44 | 30 | 30 | 42 | 45 | 12 |
| Glucose Infused | | | | | | | | |
| 19 | | 248.08 | 253.42 | 204.32 | 274.18 | 293.32 | 197.72 | 302.82 |
| 20 | | 273.42 | 359.34 | 299.12 | 249.46 | 270.78 | 270.16 | 307.94 |
| 21 | | 82.4 | 395.08 | 287.6 | 312.9 | 241.88 | 195.3 | 179.52 |
| 22 | | 75.94 | 41.7 | 82.94 | 41.04 | −45.9 | −72.7 | 10.3 |
| 23 | | 56.56 | 177.98 | 276.5 | 209.14 | 336.32 | 256.5 | 255.78 |
| 24 | | 262.72 | 274.48 | 335.28 | 314.44 | 191.4 | 113.62 | 88.96 |
| 25 | | 195.1 | 231.16 | 272.56 | 318.22 | 287.62 | 300.54 | 281.16 |
| 26 | | −49.6 | 134.56 | 137.6 | 241.98 | 370.1 | 350.42 | 337.68 |
| 27 | | 210.76 | 243.38 | 59.54 | 266.56 | 290.3 | 284.88 | 208.32 |
| AVERAGE | | 151 | 235 | 217 | 248 | 248 | 211 | 219 |
| S.E.M. | | 38 | 36 | 34 | 29 | 41 | 42 | 37 |

TABLE 10

| | Rats Daily Body Weights in Grams | | | | | | | |
|---|---|---|---|---|---|---|---|---|
| | PAIR-FED CONTROL: 0.9% NaCl | | | | | | | |
| RAT | DAY | | | | | | | |
| NUMBER | 0 | 1 | 2 | 3 | 4 | 5 | 6 | 7 |
| 1 | 236 | 229 | 225 | 232 | 242 | 241 | 240 | 230 |
| 2 | 228 | 231 | 233 | 231 | 230 | 232 | 226 | 224 |
| 3 | 240 | 237 | 235 | 235 | 233 | 213 | 205 | 199 |
| 4 | 265 | 264 | 264 | 261 | 258 | 256 | 255 | 257 |
| 5 | 234 | 235 | 238 | 243 | 252 | 258 | 259 | 266 |
| 6 | 272 | 261 | 263 | 263 | 262 | 253 | 249 | 243 |
| 7 | 244 | 243 | 244 | 243 | 248 | 247 | 250 | 244 |
| 8 | 258 | 250 | 247 | 252 | 257 | 258 | 258 | 255 |
| 9 | 212 | 204 | 207 | 206 | 194 | 195 | 190 | 181 |
| AVERAGE | 243 | 239 | 240 | 241 | 242 | 239 | 237 | 233 |
| S.E.M. | 6 | 6 | 6 | 6 | 7 | 7 | 8 | 9 |
| 1-Acetoacetamido-2,3-propanediol | | | | | | | | |
| 10 | 247 | 243 | 247 | 251 | 255 | 253 | 251 | 250 |
| 11 | 223 | 207 | 205 | 204 | 199 | 246 | 242 | 218 |
| 12 | 252 | 240 | 239 | 238 | 234 | 234 | 233 | 232 |
| 13 | 251 | 230 | 227 | 223 | 208 | 212 | 204 | 196 |
| 14 | 259 | 244 | 243 | 240 | 255 | 230 | 243 | 232 |
| 15 | 252 | 242 | 239 | 238 | 235 | 241 | 248 | 237 |
| 16 | 236 | 227 | 230 | 243 | 233 | 236 | 232 | 219 |
| 17 | 243 | 239 | 235 | 235 | 233 | 237 | 233 | 232 |
| 18 | 237 | 237 | 237 | 233 | 244 | 234 | 231 | 236 |
| AVERAGE | 244 | 234 | 234 | 234 | 233 | 236 | 235 | 228 |
| S.E.M. | 4 | 4 | 4 | 5 | 6 | 4 | 5 | 5 |
| Glucose Infused | | | | | | | | |
| 19 | 254 | 247 | 261 | 260 | 263 | 268 | 263 | 264 |
| 20 | 288 | 292 | 290 | 292 | 297 | 298 | 302 | 305 |
| 21 | 263 | 256 | 267 | 269 | 273 | 270 | 267 | 272 |
| 22 | 251 | 247 | 246 | 240 | 239 | 237 | 241 | 237 |
| 23 | 227 | 225 | 224 | 227 | 234 | 239 | 259 | 247 |
| 24 | 260 | 259 | 259 | 264 | 282 | 270 | 268 | 261 |
| 25 | 249 | 241 | 237 | 244 | 248 | 250 | 254 | 249 |
| 26 | 233 | 227 | 235 | 234 | 239 | 241 | 245 | 244 |
| 27 | 247 | 244 | 245 | 229 | 245 | 239 | 271 | 255 |
| AVERAGE | 252 | 249 | 252 | 251 | 258 | 257 | 263 | 259 |
| S.E.M. | 6 | 7 | 7 | 7 | 7 | 7 | 6 | 7 |

TABLE 11

| Rat Number | Liver Wt. | Liver/ 100 GM | mg/dl Glucose | mMOL/L ACAC | mMOL/L BOHB | mmol/L Total FFA |
|---|---|---|---|---|---|---|
| 1 | 9.0537 | 3.936391 | 109.8 | 0.0958 | 0.8481 | 0.306 |
| 2 | 7.3344 | 3.274285 | 96.3 | 0.1141 | 0.8658 | 0.749 |
| 3 | 5.3402 | 2.683517 | 111 | 0.1308 | 0.3883 | 0.313 |
| 4 | 8.9487 | 3.481984 | 116.2 | 0.15 | 0.5818 | 0.554 |
| 5 | 11.6123 | 4.365526 | 118.1 | 0.0074 | 0.2415 | 0.251 |
| 6 | 7.322 | 3.013168 | 130.2 | 0.3283 | 0.9325 | 0.479 |
| 7 | 8.4468 | 3.461803 | 133.4 | 0.1223 | 0.6325 | 0.58 |
| 8 | 8.4174 | 3.300941 | 145.5 | 0.1701 | 0.8272 | 0.52 |
| 9 | 7.3726 | 4.073259 | 128 | 0.1476 | 0.8847 | 0.735 |
| AVERAGE | 8.205 | 3.510 | 120.1044 | 0.141 | 0.689 | 0.499 |
| S.E.M. | 0.570 | 0.177 | 4.937 | 0.028 | 0.082 | 0.060 |
| 10 | 9.0537 | 3.62148 | 109.8 | 0.0958 | 0.8481 | 0.306 |
| 11 | 11.2604 | 5.165321 | 105.2 | 0.1231 | 0.9004 | 0.472 |
| 12 | 9.1128 | 3.927931 | 112.1 | | 0.2501 | 0.376 |
| 13 | 7.3291 | 3.739336 | 111.4 | 0.1385 | 1.13 | 1.408 |
| 14 | 9.3228 | 4.018448 | 121 | 0.1032 | 0.8685 | 0.546 |
| 15 | 7.2672 | 3.066329 | 91.1 | 0.3378 | 1.3611 | 0.651 |
| 16 | 9.4265 | 4.304337 | 132.1 | 0.0999 | 0.5709 | 0.286 |
| 17 | 7.4879 | 3.227543 | 114.6 | 0.3415 | 1.163 | 0.676 |
| 18 | 9.3213 | 3.949703 | 80 | 0.3225 | 0.9826 | 0.498 |
| AVERAGE | 8.842 | 3.891 | 108.589 | 0.195 | 0.897 | 0.580 |
| S.E.M. | 0.431 | 0.205 | 5.136 | 0.041 | 0.110 | 0.113 |
| 19 | 8.2264 | 3.116060 | 263.3 | 0.0085 | 0.5282 | 0.327 |
| 20 | 11.4311 | 3.747901 | 203.5 | 0.1195 | 0.5088 | 0.231 |
| 21 | 9.5132 | 3.4975 | 429.3 | 0.0177 | 0.5936 | 0.462 |
| 22 | 8.9798 | 3.788945 | 208 | | 0.2075 | 0.434 |
| 23 | 9.9056 | 4.010364 | 284.8 | 0.0095 | 0.6958 | 0.525 |
| 24 | 12.0506 | 4.617088 | 163.5 | | 0.6475 | 0.303 |
| 25 | 8.4742 | 3.403293 | 124.9 | 0.0038 | 0.3727 | 0.206 |
| 26 | 8.2387 | 3.376516 | 136 | | 0.4066 | 0.395 |
| 27 | 8.0815 | 3.169215 | 116.6 | 0.0145 | 0.651 | 0.19 |
| AVERAGE | 9.433 | 3.636 | 214.433 | 0.029 | 0.512 | 0.341 |
| S.E.M. | 0.485 | 0.157 | 33.334 | 0.018 | 0.053 | 0.040 |

We claim:

1. A parenteral nutrient solution composition comprising a sterile aqueous solution of an effective amount of at least one glycerol bisacetoacetate of the formula:

wherein one R group is hydrogen, and two R groups are $-COCH_2COCH_3$).

2. The composition according to claim 1 wherein the solution contains about 1 to 25 weight % of said glycerol bisacetoacetate.

3. The composition according to claim 1 wherein the glycerol bisacetoacetate is a mixture of 1,3- and 1,2-bisacetoacetyl glycerol.

4. The composition according to claim 3 wherein said glycerol bisacetoacetate also contains a minor amount of trisacetoacetyl glycerol dissolved into solution.

5. The composition according to claim 1 wherein said glycerol bisacetoacetate is at least 50% of the 1,3 isomer.

6. A process for administration of a parenteral nutrient solution to a body comprising introducing the parenteral nutrient solution of claim 1 into a vein of a mammal.

7. The composition according to claim 1 wherein the effective amount in said aqueous solution of said glycerol bisacetoacetate is about 5 to 15 weight percent.

* * * * *